(12) United States Patent
Booth et al.

(10) Patent No.: US 11,746,140 B2
(45) Date of Patent: Sep. 5, 2023

(54) COMPOSITION COMPRISING RECOMBINANT GPLBα RECEPTOR PROTEIN

(71) Applicant: Grifols Diagnostic Solutions Inc., Emeryville, CA (US)

(72) Inventors: Elizabeth Booth, Berkeley, CA (US); Virginia Montanini, L'Ametlla del Valles (ES); John A. Hall, Rohnert Park, CA (US); Jody Berry, Easton, PA (US)

(73) Assignee: F. HOFFMAN-LA ROCHE AG, Basel (CH)

( * ) Notice: Subject to any disclaimer, the term of this patent is extended or adjusted under 35 U.S.C. 154(b) by 0 days.

(21) Appl. No.: 16/479,068

(22) PCT Filed: Feb. 15, 2019

(86) PCT No.: PCT/IB2019/051227
§ 371 (c)(1),
(2) Date: Jul. 18, 2019

(87) PCT Pub. No.: WO2019/162813
PCT Pub. Date: Aug. 29, 2019

(65) Prior Publication Data
US 2022/0033473 A1 Feb. 3, 2022

Related U.S. Application Data

(60) Provisional application No. 62/632,870, filed on Feb. 20, 2018.

(51) Int. Cl.
*C07K 14/705* (2006.01)
*C07K 14/745* (2006.01)

(52) U.S. Cl.
CPC .......... *C07K 14/745* (2013.01); *C07K 14/705* (2013.01); *C07K 2317/92* (2013.01); *C07K 2319/02* (2013.01); *C07K 2319/21* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 8,163,496 | B2 | 4/2012 | Montgomery |
| 8,592,557 | B2 | 11/2013 | Hill et al. |
| 8,932,820 | B2 | 1/2015 | Althaus et al. |
| 9,046,535 | B2 | 6/2015 | Montgomery |
| 2003/0232047 | A1 | 12/2003 | Shaw et al. |
| 2005/0019224 | A1 | 1/2005 | Pechter et al. |
| 2006/0093614 | A1 | 5/2006 | Shaw et al. |
| 2007/0274999 | A1 | 11/2007 | Shaw |
| 2010/0120172 | A1 | 5/2010 | Fukuchi et al. |
| 2015/0260736 | A1 | 9/2015 | Patzke |
| 2016/0231331 | A1 | 8/2016 | Althaus et al. |

FOREIGN PATENT DOCUMENTS

| | | |
|---|---|---|
| CN | 101755211 A | 6/2010 |
| CN | 104914246 A | 9/2015 |
| EP | 1074564 B1 | 12/2008 |
| EP | 2167978 A2 | 3/2010 |
| JP | 2005-73528 A | 3/2005 |
| JP | 2007-537710 A | 12/2007 |
| JP | 2010-532467 A | 10/2010 |
| WO | 02063003 A2 | 8/2002 |
| WO | 2004/111089 A2 | 12/2004 |
| WO | 2009/007051 A2 | 1/2009 |
| WO | 2019/030581 A1 | 2/2019 |

OTHER PUBLICATIONS

Japanese Office Action dated Jun. 14, 2021 in corresponding Japanese Patent Application No. 2019-533522 (29 pages total).
European Office Action dated Nov. 18, 2020 in corresponding European Patent Application No. 19709125.9 (11 pages total).
Harbury, P.B. et al., "A switch between two-, three-, and four-stranded coiled coils in GCN4 leucine zipper mutants", Science (1993) 262:1401.
Miller, J. L. et al., "Mutation in the gene encoding the a chain of platelet glycoprotein Ib in platelet-type von Willebrand disease," Proc. Natl. Acad. Sci. U. S. A., vol. 88, No. June, pp. 4761-4765, 1991.
Russell, S. D. et al., "Pseudo-von Willebrand Disease: A Mutation in the Platelet Glycoprotein Ibα Gene Associated With a Hyperactive Surface Receptor," Blood, vol. 81, No. 7, pp. 1787-1792, 1993.
Hamilton, A. et al., "Frequency of Platelet type versus Type 2B von Willebrand Disease An international registry-based study," Thromb. Haemost., vol. 105, pp. 501-508, 2011.
Enayat, S. et al., "A novel D235Y mutation in the GP1BA gene enhances platelet interaction with von Willebrand factor in an Iranian family with platelet-type von Willebrand disease," Thromb. Haemost., vol. 108, No. 5, pp. 946-954, 2012.
Woods, A. I. et al., "Identification of p. W246L As a Novel Mutation in the GP1BA Gene Responsible for Platelet-Type von Willebrand Disease," Semin. Thromb. Hemost., vol. 40, pp. 151-160, 2014.
Lavenu-Bombled, C et al., "A novel platelet-type von Willebrand disease mutation (GP1BA p. Met255Ile) associated with type 2B 'Malmo / New York' von Willebrand disease," Thromb. Haemost., vol. 105, No. 3, pp. 501-508, 2016.

(Continued)

*Primary Examiner* — Christine J Saoud
*Assistant Examiner* — Jon M Lockard
(74) *Attorney, Agent, or Firm* — Dinsmore & Shohl LLP

(57) ABSTRACT

Various aspects of the invention relate to recombinant polypeptides that specifically bind human von Willebrand Factor. Such recombinant polypeptides typically include a modified extracellular domain of platelet glycoprotein Ibα that typically comprises at least one mutation selected from G233T, D235V, and K237V, and such recombinant polypeptides optionally include an oligomerization domain.

Figure 1:
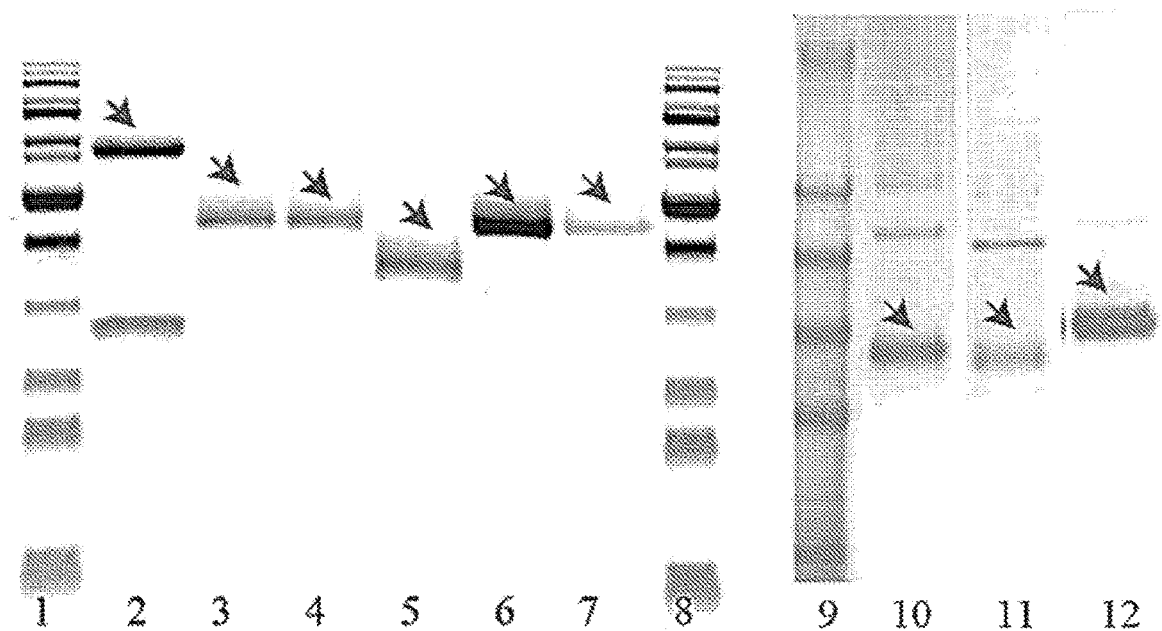

26 Claims, 4 Drawing Sheets
Specification includes a Sequence Listing.

(56) References Cited

OTHER PUBLICATIONS

"Human glycoprotein Ib/mouse IgG1Fc chimeric protein", XP55747057, retrieved from EBI accession No. GSP: AAY49933 Database accession No. AAY49933—Sep. 12, 2003.

"Glycoprotein GPIb2V variant #3", XP055747055, retrieved from EBI accesssion No. GSP: ANZ22224 Database accession No. ANZ22224—Jan. 24, 2008.

Madabhushi, S.R. et al., "Platelet GpIbα Binding to von Willebrand Factor Under Fluid Shear: Contributions of the D'D3-Domain, A1-Domain Flanking Peptide and O-Linked Glycans", Journal American Heart Association, (2014), vol. 3, e001420 (pp. 1-13).

Wright, G.J., "Signal initiation in biological systems: the properties and detection of transient extracellular protein interactions", Molecular BioSystems, (2009), vol. 5, pp. 1405-1412.

Czajkowsky, D.M. et al., "Fc-fusion proteins: new developments and future perspectives", EMBO Mol. Med., (2012), vol. 4, pp. 1015-1028.

Flood, V.H. et al., "Gain-of-function GPIb ELISA assay for VWF activity in the Zimmerman Program for the Molecular and Clinical Biology of VWD", Blood, (2011), vol. 117, No. 6, pp. e67-e74.

Patzke, J. et al., "Performance evaluation and multicentre study of a von Willebrand factor activity assay based on GPIb binding in the absence of ristocetin", Blood Coagulation & Fibrinolysis, (2014), vol. 25, 8, pp. 860-870.

Graf, L. et al., "Evaluation of an automated method for measuring von Willebrand factor activity in clinical samples without ristocetin", International Journal of Laboratory Hematology, (2014), vol. 36, pp. 341-351.

Lopez, J.A. et al., "Cloning of the alpha chain of human platelet glycoprotein Ib: a transmembrane protein with homology to leucine-rich alpha 2-glycoprotein", Proceedings of the National Academy of Sciences of America, USA, (1987), vol. 84, pp. 5615-5619.

Sliepen, K. et al., "Immunosilencing a Highly Immunogenic Protein Trimerization Domain" Journal Biological Chemistry, (2015), vol. 290, No. 12, pp. 7436-7442.

Meier, S. et al., "Foldon, The Natural Trimerization Domain of T4 Fibritin, Dissociates into a Monomeric A-state Form containing a Stable β-Hairpin: Atomic Details of Trimer Dissociation and Local β-Hairpin Stability from Residual Dipolar Couplings", Journal of Molecular Biology, (2004), vol. 344, pp. 1051-1069.

Japanese Office Action dated Jul. 13, 2020 in corresponding Japanese Patent Application No. 2019-533522 (19 pages total).

Shuji Miura et al., "Interaction of von Willebrand Factor Domain A1 with Platelet Glycoprotein Ibα-(1-289)", The Journal of Biological Chemistry, vol. 275, No. 11, Mar. 17, 2000, pp. 7539-7546.

Patrizia Marchese et al., "Adhesive properties of the isolated amino-terminal domain of platelet glycoprotein Ibα in a flow field", Proc. Natl. Acad. Sci., vol. 96, Jul. 1999, pp. 7837-7842.

Y. Matsubara et al., "Identification of a novel point mutation in platelet glycoprotein Ibα, Gly to Ser at residue 233, in a Japanese family with platelet-type von Willebrand disease", Journal of Thrombosis and Haemostasis, vol. 1, pp. 2198-2205.

Qingsheng Huang et al., "Conformational Transition of Glycoprotein Ibα Mutants in Flow Molecular Dynamics Simulation", Cellular and Molecular Bioengineering, vol. 4, No. 3, Sep. 2011, pp. 495-504.

Mohammad S. Enayat et al., "Distinguishing between type 2B and pseudo-von Willebrand disease and its clinical importance", British Journal of Haematology, vol. 133, 2006, pp. 664-666.

International Search Report and Written Opinion dated Jul. 3, 2019 in related international Application No. PCT/IB2019/051227 (21 pages total).

Jing-fei Dong et al., "Novel Gain-of-function Mutations of Platelet Glycoprotein Ibα by Valine Mutagenesis in the Cys209-Cys248 Disulfide Loop: Functional Analysis Under Static and Dynamic Conditions", The Journal of Biological Chemistry, vol. 275, No. 36, Issue Sep. 8, 2000, pp. 27663-27670, XP00222663.

R. Anand Kumar et al., "Kinetics of GPIbα-vWF-A1 Tether Bond under Flow: Effect of GPIbα Mutations on the Association and Dissociation Rates", Biophysical Journal, vol. 85, Dec. 2003, pp. 4099-4109.

Hampsire DJ, Burghel GJ, Goudemand J, Bouvet LCS, Eikenboom JCJ; Polymorphic variation within the VWF gene contributes to the failure to detect mutations in patients historically diagnosed with type 1 von Willebrand disease from the MCMDM-1VWD cohort; Issue: vol. 95 No. 12 (2010): Dec. 2010DOI.

Office action dated Nov. 28, 2022 in related Korean Patent Application No. 10-2021-7035205 filed Oct. 28, 2021.

Office action dated Jan. 27, 2023 in related Colombian Patent Application No. NC2020/0011377 filed Feb. 15, 2019.

Office Action issued by Taiwanese Trade Mark and Patent Office in correspondence to Chinese Application No. 108105202.

SEQUENCE LISTING

```
<160> NUMBER OF SEQ ID NOS: 46

<210> SEQ ID NO 1
<211> LENGTH: 290
<212> TYPE: PRT
<213> ORGANISM: Artificial Sequence
<220> FEATURE:
<223> OTHER INFORMATION: Synthetic

<400> SEQUENCE: 1

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30
```

Thr Thr Ile Leu His Leu Ser Glu Asn Leu Leu Tyr Thr Phe Ser Leu
            35                  40                  45

Ala Thr Leu Met Pro Tyr Thr Arg Leu Thr Gln Leu Asn Leu Asp Arg
 50                  55                  60

Ser Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
            115                 120                 125

Leu Tyr Leu Lys Gly Asn Glu Leu Lys Thr Leu Pro Pro Gly Leu Leu
            130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
            195                 200                 205

Cys Asn Cys Glu Ile Leu Tyr Phe Arg Arg Trp Leu Gln Asp Asn Ala
            210                 215                 220

Glu Asn Val Tyr Val Trp Lys Gln Gly Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
            275                 280                 285

Val Arg
 290

<210> SEQ ID NO 2
<211> LENGTH: 290
<212> TYPE: PRT
<213> ORGANISM: Artificial Sequence
<220> FEATURE:
<223> OTHER INFORMATION: Synthetic Construct

<400> SEQUENCE: 2

His Pro Ile Cys Glu Val Ser Lys Val Ala Ser His Leu Glu Val Asn
 1               5                  10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
            35                  40                  45

Ala Thr Leu Met Pro Tyr Thr Arg Leu Thr Gln Leu Asn Leu Asp Arg
 50                  55                  60

Ser Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                85                  90                  95

```
Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
            115                 120                 125

Leu Tyr Leu Lys Gly Asn Glu Leu Lys Thr Leu Pro Pro Gly Leu Leu
            130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
            195                 200                 205

Cys Asn Cys Glu Ile Leu Tyr Phe Arg Arg Trp Leu Gln Asp Asn Ala
            210                 215                 220

Glu Asn Val Tyr Val Trp Lys Gln Gly Val Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
            275                 280                 285

Val Arg
    290

<210> SEQ ID NO 3
<211> LENGTH: 290
<212> TYPE: PRT
<213> ORGANISM: Artificial Sequence
<220> FEATURE:
<223> OTHER INFORMATION: Synthetic Construct

<400> SEQUENCE: 3

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
            35                  40                  45

Ala Thr Leu Met Pro Tyr Thr Arg Leu Thr Gln Leu Asn Leu Asp Arg
        50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
            115                 120                 125

Leu Tyr Leu Lys Gly Asn Glu Leu Lys Thr Leu Pro Pro Gly Leu Leu
            130                 135                 140

Thr Pro Thr Pro Lys Leu Glu Lys Leu Ser Leu Ala Asn Asn Asn Leu
145                 150                 155                 160
```

```
Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Gly Val Asp Val Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
                260                 265                 270

Thr Asp Leu Tyr Asp Tyr Tyr Pro Glu Glu Asp Thr Glu Gly Asp Lys
            275                 280                 285

Val Arg
    290

<210> SEQ ID NO 4
<211> LENGTH: 290
<212> TYPE: PRT
<213> ORGANISM: Artificial Sequence
<220> FEATURE:
<223> OTHER INFORMATION: Synthetic

<400> SEQUENCE: 4

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
                20                  25                  30

Thr Thr Ile Leu His Leu Ser Glu Asn Leu Leu Tyr Thr Phe Ser Leu
            35                  40                  45

Ala Thr Leu Met Pro Tyr Thr Arg Leu Thr Gln Leu Asn Leu Asp Arg
    50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220
```

```
Glu Asn Val Tyr Val Trp Lys Gln Thr Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg
    290

<210> SEQ ID NO 5
<211> LENGTH: 290
<212> TYPE: PRT
<213> ORGANISM: Artificial Sequence
<220> FEATURE:
<223> OTHER INFORMATION: Synthetic

<400> SEQUENCE: 5

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
                20                  25                  30

Thr Thr Ile Leu His Leu Ser Glu Asn Leu Leu Tyr Thr Phe Ser Leu
            35                  40                  45

Ala Thr Leu Met Pro Tyr Thr Arg Leu Thr Gln Leu Asn Leu Asp Arg
    50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Thr Val Asp Val Lys Ala Thr Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285
```

Val Arg
    290

<210> SEQ ID NO 6
<211> LENGTH: 290
<212> TYPE: PRT
<213> ORGANISM: Artificial Sequence
<220> FEATURE:
<223> OTHER INFORMATION: Synthetic

<400> SEQUENCE: 6

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Gly Val Asp Val Lys Val Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg
    290

<210> SEQ ID NO 7
<211> LENGTH: 290
<212> TYPE: PRT
<213> ORGANISM: Artificial Sequence
<220> FEATURE:
<223> OTHER INFORMATION: Synthetic

<400> SEQUENCE: 7

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Pro Glu Glu Asp Thr Glu Gly Asp Lys
        275                 280                 285

Val Arg
    290

<210> SEQ ID NO 8
<211> LENGTH: 290
<212> TYPE: PRT
<213> ORGANISM: Artificial Sequence
<220> FEATURE:
<223> OTHER INFORMATION: Synthetic

<400> SEQUENCE: 8

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg

```
            50                  55                  60
Ser Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                 85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Val Asp Val Lys Ala Val Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Pro Glu Glu Asp Thr Glu Gly Asp Lys
        275                 280                 285

Val Arg
    290

<210> SEQ ID NO 9
<211> LENGTH: 278
<212> TYPE: PRT
<213> ORGANISM: Artificial Sequence
<220> FEATURE:
<223> OTHER INFORMATION: Synthetic

<400> SEQUENCE: 9

His Pro Ile Cys Glu Val Ser Lys Val Ala Ser His Leu Glu Val Asn
 1               5                  10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Ser Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                 85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
```

```
                115                 120                 125
Leu Tyr Leu Lys Gly Asn Glu Leu Lys Thr Leu Pro Pro Gly Leu Leu
        130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
        210                 215                 220

Glu Asn Val Tyr Ser Asn Val Ala Ser Val Gln Cys Asp Asn Ser Asp
225                 230                 235                 240

Lys Phe Pro Val Tyr Lys Tyr Pro Gly Lys Gly Cys Pro Thr Leu Gly
                245                 250                 255

Asp Glu Gly Asp Thr Asp Leu Tyr Asp Tyr Tyr Pro Glu Glu Asp Thr
            260                 265                 270

Glu Gly Asp Lys Val Arg
        275

<210> SEQ ID NO 10
<211> LENGTH: 40
<212> TYPE: PRT
<213> ORGANISM: Artificial Sequence
<220> FEATURE:
<223> OTHER INFORMATION: Synthetic

<400> SEQUENCE: 10

Lys Pro Leu Asp Gly Glu Tyr Phe Thr Leu Gln Ile Arg Gly Arg Glu
1               5                   10                  15

Arg Phe Glu Met Phe Arg Glu Leu Asn Glu Ala Leu Glu Leu Lys Asp
            20                  25                  30

Ala Gln Ala Gly Lys Glu Pro Gly
        35                  40

<210> SEQ ID NO 11
<211> LENGTH: 227
<212> TYPE: PRT
<213> ORGANISM: Artificial Sequence
<220> FEATURE:
<223> OTHER INFORMATION: Synthetic

<400> SEQUENCE: 11

Val Pro Arg Asp Cys Gly Cys Lys Pro Cys Ile Cys Thr Val Pro Glu
1               5                   10                  15

Val Ser Ser Val Phe Ile Phe Pro Pro Lys Pro Lys Asp Val Leu Thr
            20                  25                  30

Ile Thr Leu Thr Pro Lys Val Thr Cys Val Val Val Asp Ile Ser Lys
        35                  40                  45

Asp Asp Pro Glu Val Gln Phe Ser Trp Phe Val Asp Asp Val Glu Val
    50                  55                  60

His Thr Ala Gln Thr Gln Pro Arg Glu Glu Gln Phe Asn Ser Thr Phe
65                  70                  75                  80

Arg Ser Val Ser Glu Leu Pro Ile Met His Gln Asp Trp Leu Asn Gly
                85                  90                  95
```

```
Lys Glu Phe Lys Cys Arg Val Asn Ser Ala Ala Phe Pro Ala Pro Ile
                100                 105                 110

Glu Lys Thr Ile Ser Lys Thr Lys Gly Arg Pro Lys Ala Pro Gln Val
            115                 120                 125

Tyr Thr Ile Pro Pro Pro Lys Glu Gln Met Ala Lys Asp Lys Val Ser
130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Asp Thr Asp Gly Ser Tyr Phe Val Tyr Ser Lys Leu Asn Val
            180                 185                 190

Gln Lys Ser Asn Trp Glu Ala Gly Asn Thr Phe Thr Cys Ser Val Leu
        195                 200                 205

His Glu Gly Leu His Asn His His Thr Glu Lys Ser Leu Ser His Ser
    210                 215                 220

Pro Gly Ile
225

<210> SEQ ID NO 12
<211> LENGTH: 231
<212> TYPE: PRT
<213> ORGANISM: Artificial Sequence
<220> FEATURE:
<223> OTHER INFORMATION: Synthetic

<400> SEQUENCE: 12

Pro Arg Gly Pro Thr Ile Lys Pro Cys Pro Pro Cys Lys Cys Pro Ala
1               5                   10                  15

Pro Asn Leu Leu Gly Gly Pro Ser Val Phe Ile Phe Pro Pro Lys Ile
            20                  25                  30

Lys Asp Val Leu Met Ile Ser Leu Ser Pro Ile Val Thr Cys Val Val
        35                  40                  45

Val Asp Val Ser Glu Asp Asp Pro Asp Val Gln Ile Ser Trp Phe Val
    50                  55                  60

Asn Asn Val Glu Val His Thr Ala Gln Thr Gln Thr His Arg Glu Asp
65                  70                  75                  80

Tyr Asn Ser Thr Leu Arg Val Val Ser Ala Leu Pro Ile Gln His Gln
                85                  90                  95

Asp Trp Met Ser Gly Lys Glu Phe Lys Cys Lys Val Asn Asn Lys Asp
            100                 105                 110

Leu Pro Ala Pro Ile Glu Arg Thr Ile Ser Lys Pro Lys Gly Ser Val
        115                 120                 125

Arg Ala Pro Gln Val Tyr Val Leu Pro Pro Pro Glu Glu Glu Met Thr
130                 135                 140

Lys Lys Gln Val Thr Leu Thr Cys Met Val Thr Asp Phe Met Pro Glu
145                 150                 155                 160

Asp Ile Tyr Val Glu Trp Thr Asn Asn Gly Lys Thr Glu Leu Asn Tyr
                165                 170                 175

Lys Asn Thr Glu Pro Val Leu Asp Ser Asp Gly Ser Tyr Phe Met Tyr
            180                 185                 190

Ser Lys Leu Arg Val Glu Lys Lys Asn Trp Val Glu Arg Asn Ser Tyr
        195                 200                 205

Ser Cys Ser Val Val His Glu Gly Leu His Asn His Thr Thr Lys
210                 215                 220
```

Ser Phe Ser Arg Thr Pro Gly
225                 230

<210> SEQ ID NO 13
<211> LENGTH: 27
<212> TYPE: PRT
<213> ORGANISM: Artificial Sequence
<220> FEATURE:
<223> OTHER INFORMATION: Synthetic

<400> SEQUENCE: 13

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 14
<211> LENGTH: 94
<212> TYPE: PRT
<213> ORGANISM: Artificial Sequence
<220> FEATURE:
<223> OTHER INFORMATION: Synthetic

<400> SEQUENCE: 14

Gly Ser His Met Trp Lys Gln Ser Val Glu Leu Ala Lys Lys Asp Ser
1               5                   10                  15

Leu Tyr Lys Asp Ala Met Gln Tyr Ala Ser Glu Ser Lys Asp Thr Glu
            20                  25                  30

Leu Ala Glu Glu Leu Leu Gln Trp Phe Leu Gln Glu Glu Lys Arg Glu
        35                  40                  45

Cys Phe Gly Ala Cys Leu Phe Thr Cys Tyr Asp Leu Leu Arg Pro Asp
    50                  55                  60

Val Val Leu Glu Leu Ala Trp Arg His Asn Ile Met Asp Phe Ala Met
65                  70                  75                  80

Pro Tyr Phe Ile Gln Val Met Lys Glu Tyr Leu Thr Lys Val
                85                  90

<210> SEQ ID NO 15
<211> LENGTH: 6
<212> TYPE: PRT
<213> ORGANISM: Artificial Sequence
<220> FEATURE:
<223> OTHER INFORMATION: Synthetic

<400> SEQUENCE: 15

His His His His His His
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

His His His His His His Cys
1               5

<210> SEQ ID NO 17
<211> LENGTH: 21
<212> TYPE: PRT
<213> ORGANISM: Artificial Sequence
<220> FEATURE:

<223> OTHER INFORMATION: Synthetic

<400> SEQUENCE: 17

Glu Glu Ala Ala Glu Glu Ala Ala Glu Glu Ser Asp Asp Asp His
1               5                   10                  15

His His His His His
            20

<210> SEQ ID NO 18
<211> LENGTH: 44
<212> TYPE: PRT
<213> ORGANISM: Artificial Sequence
<220> FEATURE:
<223> OTHER INFORMATION: Synthetic

<400> SEQUENCE: 18

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro His His His His His His
        35                  40

<210> SEQ ID NO 19
<211> LENGTH: 290
<212> TYPE: PRT
<213> ORGANISM: Homo sapiens

<400> SEQUENCE: 19

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Cys Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

```
Glu Asn Val Tyr Val Trp Lys Gln Gly Val Asp Val Lys Ala Met Thr
225                 230                 235                 240

Ser Asn Val Ala Ser Val Gln Cys Asp Asn Ser Asp Lys Phe Pro Val
            245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg
    290

<210> SEQ ID NO 20
<211> LENGTH: 25
<212> TYPE: PRT
<213> ORGANISM: Homo sapiens

<400> SEQUENCE: 20

Met Asp Ala Met Lys Arg Gly Leu Cys Cys Val Leu Leu Leu Cys Gly
1               5                   10                  15

Ala Val Phe Val Ser Pro Ser Ala Ser
            20                  25

<210> SEQ ID NO 21
<211> LENGTH: 526
<212> TYPE: PRT
<213> ORGANISM: Artificial Sequence
<220> FEATURE:
<223> OTHER INFORMATION: Synthetic

<400> SEQUENCE: 21

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
            35                  40                  45

Ala Thr Leu Met Pro Tyr Thr Arg Leu Thr Gln Leu Asn Leu Asp Arg
    50                  55                  60

Ser Glu Leu Thr Lys Leu Gln Val Asp Gly Thr Leu Pro Val Leu Gly
65              70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
            115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
            195                 200                 205

Cys Asn Cys Glu Ile Leu Tyr Phe Arg Arg Trp Leu Gln Asp Asn Ala
```

```
            210                 215                 220
Glu Asn Val Tyr Val Trp Lys Gln Thr Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Pro Glu Glu Asp Thr Glu Gly Asp Lys
        275                 280                 285

Val Arg Val Pro Arg Asp Cys Gly Cys Lys Pro Cys Ile Cys Thr Val
    290                 295                 300

Pro Glu Val Ser Ser Val Phe Ile Phe Pro Lys Pro Lys Asp Val
305                 310                 315                 320

Leu Thr Ile Thr Leu Thr Pro Lys Val Thr Cys Val Val Asp Ile
                325                 330                 335

Ser Lys Asp Asp Pro Glu Val Gln Phe Ser Trp Phe Val Asp Asp Val
                340                 345                 350

Glu Val His Thr Ala Gln Thr Gln Pro Arg Glu Glu Gln Phe Asn Ser
            355                 360                 365

Thr Phe Arg Ser Val Ser Glu Leu Pro Ile Met His Gln Asp Trp Leu
        370                 375                 380

Asn Gly Lys Glu Phe Lys Cys Arg Val Asn Ser Ala Ala Phe Pro Ala
385                 390                 395                 400

Pro Ile Glu Lys Thr Ile Ser Lys Thr Lys Gly Arg Pro Lys Ala Pro
                405                 410                 415

Gln Val Tyr Thr Ile Pro Pro Lys Glu Gln Met Ala Lys Asp Lys
            420                 425                 430

Val Ser Leu Thr Cys Met Ile Thr Asp Phe Phe Pro Glu Asp Ile Thr
                435                 440                 445

Val Glu Trp Gln Trp Asn Gly Gln Pro Ala Glu Asn Tyr Lys Asn Thr
            450                 455                 460

Gln Pro Ile Met Asp Thr Asp Gly Ser Tyr Phe Val Tyr Ser Lys Leu
465                 470                 475                 480

Asn Val Gln Lys Ser Asn Trp Glu Ala Gly Asn Thr Phe Thr Cys Ser
                485                 490                 495

Val Leu His Glu Gly Leu His Asn His His Thr Glu Lys Ser Leu Ser
            500                 505                 510

His Ser Pro Gly Ile Gly His His His His His His
        515                 520                 525

<210> SEQ ID NO 22
<211> LENGTH: 336
<212> TYPE: PRT
<213> ORGANISM: Artificial Sequence
<220> FEATURE:
<223> OTHER INFORMATION: Synthetic

<400> SEQUENCE: 22

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
                20                  25                  30

Thr Thr Ile Leu His Leu Ser Glu Asn Leu Leu Tyr Thr Phe Ser Leu
            35                  40                  45

Ala Thr Leu Met Pro Tyr Thr Arg Leu Thr Gln Leu Asn Leu Asp Arg
```

```
                50                  55                  60
Ser Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                 85                  90                  95

Gln Thr Leu Pro Ala Leu Thr Val Leu Asp Val Ser Phe Asn Arg Leu
                100                 105                 110

Thr Ser Leu Pro Leu Gly Ala Leu Arg Gly Leu Gly Glu Leu Gln Glu
                115                 120                 125

Leu Tyr Leu Lys Gly Asn Glu Leu Lys Thr Leu Pro Pro Gly Leu Leu
            130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
                180                 185                 190

Gly Ser His Leu Leu Pro Phe Ala Phe Leu His Gly Asn Pro Trp Leu
            195                 200                 205

Cys Asn Cys Glu Ile Leu Tyr Phe Arg Arg Trp Leu Gln Asp Asn Ala
210                 215                 220

Glu Asn Val Tyr Val Trp Lys Gln Thr Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Pro Glu Glu Asp Thr Glu Gly Asp Lys
            275                 280                 285

Val Arg Lys Pro Leu Asp Gly Glu Tyr Phe Thr Leu Gln Ile Arg Gly
            290                 295                 300

Arg Glu Arg Phe Glu Met Phe Arg Glu Leu Asn Glu Ala Leu Glu Leu
305                 310                 315                 320

Lys Asp Ala Gln Ala Gly Lys Glu Pro Gly His His His His His
            325                 330                 335

<210> SEQ ID NO 23
<211> LENGTH: 336
<212> TYPE: PRT
<213> ORGANISM: Artificial Sequence
<220> FEATURE:
<223> OTHER INFORMATION: Synthetic

<400> SEQUENCE: 23

His Pro Ile Cys Glu Val Ser Lys Val Ala Ser His Leu Glu Val Asn
 1               5                  10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Ser Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
```

```
                        85                  90                  95

Gln Thr Leu Pro Ala Leu Thr Val Leu Asp Val Ser Phe Asn Arg Leu
                100                 105                 110

Thr Ser Leu Pro Leu Gly Ala Leu Arg Gly Leu Gly Glu Leu Gln Glu
            115                 120                 125

Leu Tyr Leu Lys Gly Asn Glu Leu Lys Thr Leu Pro Pro Gly Leu Leu
        130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
210                 215                 220

Glu Asn Val Tyr Val Trp Lys Gln Val Val Asp Val Lys Ala Val Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg Lys Pro Leu Asp Gly Glu Tyr Phe Thr Leu Gln Ile Arg Gly
        290                 295                 300

Arg Glu Arg Phe Glu Met Phe Arg Glu Leu Asn Glu Ala Leu Glu Leu
305                 310                 315                 320

Lys Asp Ala Gln Ala Gly Lys Glu Pro Gly His His His His His
                325                 330                 335

<210> SEQ ID NO 24
<211> LENGTH: 297
<212> TYPE: PRT
<213> ORGANISM: Artificial Sequence
<220> FEATURE:
<223> OTHER INFORMATION: Synthetic

<400> SEQUENCE: 24

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
                100                 105                 110

Thr Ser Leu Pro Leu Gly Ala Leu Arg Gly Leu Gly Glu Leu Gln Glu
```

```
            115                 120                 125
Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Thr Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg His His His His His Cys
    290                 295

<210> SEQ ID NO 25
<211> LENGTH: 334
<212> TYPE: PRT
<213> ORGANISM: Artificial Sequence
<220> FEATURE:
<223> OTHER INFORMATION: Synthetic

<400> SEQUENCE: 25

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
                20                  25                  30

Thr Thr Ile Leu His Leu Ser Glu Asn Leu Leu Tyr Thr Phe Ser Leu
            35                  40                  45

Ala Thr Leu Met Pro Tyr Thr Arg Leu Thr Gln Leu Asn Leu Asp Arg
        50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
```

```
            180                 185                 190
Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Thr Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg Met Asp Glu Lys Thr Thr Gly Trp Arg Gly His Val Val
    290                 295                 300

Glu Gly Leu Ala Gly Glu Leu Glu Gln Leu Arg Ala Arg Leu Glu His
305                 310                 315                 320

His Pro Gln Gly Gln Arg Glu Pro His His His His His
                325                 330

<210> SEQ ID NO 26
<211> LENGTH: 336
<212> TYPE: PRT
<213> ORGANISM: Artificial Sequence
<220> FEATURE:
<223> OTHER INFORMATION: Synthetic

<400> SEQUENCE: 26

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Ala Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
```

```
                210                 215                 220
Glu Asn Val Tyr Val Trp Lys Gln Val Asp Val Lys Ala Val Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
                260                 265                 270

Thr Asp Leu Tyr Asp Tyr Pro Glu Glu Asp Thr Glu Gly Asp Lys
                275                 280                 285

Val Arg Lys Pro Leu Asp Gly Glu Tyr Phe Thr Leu Gln Ile Arg Gly
                290                 295                 300

Arg Glu Arg Phe Glu Met Phe Arg Glu Leu Asn Glu Ala Leu Glu Leu
305                 310                 315                 320

Lys Asp Ala Gln Ala Gly Lys Glu Pro Gly His His His His His His
                325                 330                 335

<210> SEQ ID NO 27
<211> LENGTH: 296
<212> TYPE: PRT
<213> ORGANISM: Artificial Sequence
<220> FEATURE:
<223> OTHER INFORMATION: Synthetic

<400> SEQUENCE: 27

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
                20                  25                  30

Thr Thr Ile Leu His Leu Ser Glu Asn Leu Leu Tyr Thr Phe Ser Leu
                35                  40                  45

Ala Thr Leu Met Pro Tyr Thr Arg Leu Thr Gln Leu Asn Leu Asp Arg
50                  55                  60

Ala Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
                100                 105                 110

Thr Ser Leu Pro Leu Gly Ala Leu Arg Gly Leu Gly Glu Leu Gln Glu
                115                 120                 125

Leu Tyr Leu Lys Gly Asn Glu Leu Lys Thr Leu Pro Pro Gly Leu Leu
130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
                180                 185                 190

Gly Ser His Leu Leu Pro Phe Ala Phe Leu His Gly Asn Pro Trp Leu
                195                 200                 205

Cys Asn Cys Glu Ile Leu Tyr Phe Arg Arg Trp Leu Gln Asp Asn Ala
                210                 215                 220

Glu Asn Val Tyr Val Trp Lys Gln Val Asp Val Lys Ala Val Thr
225                 230                 235                 240

Ser Asn Val Ala Ser Val Gln Cys Asp Asn Ser Asp Lys Phe Pro Val
```

```
            245                 250                 255
Tyr Lys Tyr Pro Gly Lys Gly Cys Pro Thr Leu Gly Asp Glu Gly Asp
        260                 265                 270

Thr Asp Leu Tyr Asp Tyr Tyr Pro Glu Glu Asp Thr Glu Gly Asp Lys
    275                 280                 285

Val Arg His His His His His His
    290                 295

<210> SEQ ID NO 28
<211> LENGTH: 308
<212> TYPE: PRT
<213> ORGANISM: Artificial Sequence
<220> FEATURE:
<223> OTHER INFORMATION: Synthetic

<400> SEQUENCE: 28

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Ala Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Val Val Asp Val Lys Ala Val Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Glu
        275                 280                 285

Glu Ala Ala Glu Glu Ala Ala Glu Glu Ser Asp Asp His His
    290                 295                 300

His His His His
```

<210> SEQ ID NO 29
<211> LENGTH: 313
<212> TYPE: PRT
<213> ORGANISM: Artificial Sequence
<220> FEATURE:
<223> OTHER INFORMATION: Synthetic

<400> SEQUENCE: 29

```
His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Cys Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Val Val Asp Val Lys Ala Val Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Asp Tyr Lys
        275                 280                 285

Asp His Asp Gly Asp Tyr Lys Asp His Asp Ile Asp Tyr Lys Asp Asp
    290                 295                 300

Asp Asp Lys His His His His His His
305                 310
```

<210> SEQ ID NO 30
<211> LENGTH: 526
<212> TYPE: PRT
<213> ORGANISM: Artificial Sequence
<220> FEATURE:
<223> OTHER INFORMATION: Synthetic

<400> SEQUENCE: 30

```
His Pro Ile Cys Glu Val Ser Lys Val Ala Ser His Leu Glu Val Asn
1               5                   10                  15

Cys Asp Lys Arg Asn Leu Thr Ala Leu Pro Asp Leu Pro Lys Asp
            20                  25                  30

Thr Thr Ile Leu His Leu Ser Glu Asn Leu Leu Tyr Thr Phe Ser Leu
            35                  40                  45

Ala Thr Leu Met Pro Tyr Thr Arg Leu Thr Gln Leu Asn Leu Asp Arg
    50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
                100                 105                 110

Thr Ser Leu Pro Leu Gly Ala Leu Arg Gly Leu Gly Glu Leu Gln Glu
            115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
    195                 200                 205

Cys Asn Cys Glu Ile Leu Tyr Phe Arg Arg Trp Leu Gln Asp Asn Ala
210                 215                 220

Glu Asn Val Tyr Val Trp Lys Gln Gly Val Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
            275                 280                 285

Val Arg Val Pro Arg Asp Cys Gly Cys Lys Pro Cys Ile Cys Thr Val
    290                 295                 300

Pro Glu Val Ser Ser Val Phe Ile Phe Pro Pro Lys Pro Lys Asp Val
305                 310                 315                 320

Leu Thr Ile Thr Leu Thr Pro Lys Val Thr Cys Val Val Val Asp Ile
                325                 330                 335

Ser Lys Asp Asp Pro Glu Val Gln Phe Ser Trp Phe Val Asp Asp Val
            340                 345                 350

Glu Val His Thr Ala Gln Thr Gln Pro Arg Glu Glu Gln Phe Asn Ser
    355                 360                 365

Thr Phe Arg Ser Val Ser Glu Leu Pro Ile Met His Gln Asp Trp Leu
    370                 375                 380

Asn Gly Lys Glu Phe Lys Cys Arg Val Asn Ser Ala Ala Phe Pro Ala
385                 390                 395                 400

Pro Ile Glu Lys Thr Ile Ser Lys Thr Lys Gly Arg Pro Lys Ala Pro
```

-continued

```
                405                 410                 415
Gln Val Tyr Thr Ile Pro Pro Lys Glu Gln Met Ala Lys Asp Lys
            420                 425                 430

Val Ser Leu Thr Cys Met Ile Thr Asp Phe Phe Pro Glu Asp Ile Thr
        435                 440                 445

Val Glu Trp Gln Trp Asn Gly Gln Pro Ala Glu Asn Tyr Lys Asn Thr
    450                 455                 460

Gln Pro Ile Met Asp Thr Asp Gly Ser Tyr Phe Val Tyr Ser Lys Leu
465                 470                 475                 480

Asn Val Gln Lys Ser Asn Trp Glu Ala Gly Asn Thr Phe Thr Cys Ser
                485                 490                 495

Val Leu His Glu Gly Leu His Asn His His Thr Glu Lys Ser Leu Ser
            500                 505                 510

His Ser Pro Gly Ile Gly His His His His His His
        515                 520                 525

<210> SEQ ID NO 31
<211> LENGTH: 526
<212> TYPE: PRT
<213> ORGANISM: Artificial Sequence
<220> FEATURE:
<223> OTHER INFORMATION: Synthetic

<400> SEQUENCE: 31

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Gly Val Asp Val Ala Met Thr
225                 230                 235                 240

Ser Asn Val Ala Ser Val Gln Cys Asp Asn Ser Asp Lys Phe Pro Val
```

```
                    245                 250                 255
Tyr Lys Tyr Pro Gly Lys Gly Cys Pro Thr Leu Gly Asp Glu Gly Asp
                260                 265                 270

Thr Asp Leu Tyr Asp Tyr Tyr Pro Glu Glu Asp Thr Glu Gly Asp Lys
            275                 280                 285

Val Arg Val Pro Arg Asp Cys Gly Cys Lys Pro Cys Ile Cys Thr Val
        290                 295                 300

Pro Glu Val Ser Ser Val Phe Ile Phe Pro Pro Lys Pro Lys Asp Val
305                 310                 315                 320

Leu Thr Ile Thr Leu Thr Pro Lys Val Thr Cys Val Val Val Asp Ile
                325                 330                 335

Ser Lys Asp Asp Pro Glu Val Gln Phe Ser Trp Phe Val Asp Asp Val
                340                 345                 350

Glu Val His Thr Ala Gln Thr Gln Pro Arg Glu Glu Gln Phe Asn Ser
            355                 360                 365

Thr Phe Arg Ser Val Ser Glu Leu Pro Ile Met His Gln Asp Trp Leu
        370                 375                 380

Asn Gly Lys Glu Phe Lys Cys Arg Val Asn Ser Ala Ala Phe Pro Ala
385                 390                 395                 400

Pro Ile Glu Lys Thr Ile Ser Lys Thr Lys Gly Arg Pro Lys Ala Pro
                405                 410                 415

Gln Val Tyr Thr Ile Pro Pro Pro Lys Glu Gln Met Ala Lys Asp Lys
            420                 425                 430

Val Ser Leu Thr Cys Met Ile Thr Asp Phe Phe Pro Glu Asp Ile Thr
        435                 440                 445

Val Glu Trp Gln Trp Asn Gly Gln Pro Ala Glu Asn Tyr Lys Asn Thr
    450                 455                 460

Gln Pro Ile Met Asp Thr Asp Gly Ser Tyr Phe Val Tyr Ser Lys Leu
465                 470                 475                 480

Asn Val Gln Lys Ser Asn Trp Glu Ala Gly Asn Thr Phe Thr Cys Ser
                485                 490                 495

Val Leu His Glu Gly Leu His Asn His His Thr Glu Lys Ser Leu Ser
            500                 505                 510

His Ser Pro Gly Ile Gly His His His His His His
        515                 520                 525

<210> SEQ ID NO 32
<211> LENGTH: 526
<212> TYPE: PRT
<213> ORGANISM: Artificial Sequence
<220> FEATURE:
<223> OTHER INFORMATION: Synthetic

<400> SEQUENCE: 32

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
```

-continued

```
                85                  90                  95
Gln Thr Leu Pro Ala Leu Thr Val Leu Asp Val Ser Phe Asn Arg Leu
                100                 105                 110
Thr Ser Leu Pro Leu Gly Ala Leu Arg Gly Leu Gly Glu Leu Gln Glu
                115                 120                 125
Leu Tyr Leu Lys Gly Asn Glu Leu Lys Thr Leu Pro Pro Gly Leu Leu
            130                 135                 140
Thr Pro Thr Pro Lys Leu Glu Lys Leu Ser Leu Ala Asn Asn Asn Leu
145                 150                 155                 160
Thr Glu Leu Pro Ala Gly Leu Leu Asn Gly Leu Glu Asn Leu Asp Thr
                165                 170                 175
Leu Leu Leu Gln Glu Asn Ser Leu Tyr Thr Ile Pro Lys Gly Phe Phe
            180                 185                 190
Gly Ser His Leu Leu Pro Phe Ala Phe Leu His Gly Asn Pro Trp Leu
            195                 200                 205
Cys Asn Cys Glu Ile Leu Tyr Phe Arg Arg Trp Leu Gln Asp Asn Ala
            210                 215                 220
Glu Asn Val Tyr Val Trp Lys Gln Val Val Asp Val Lys Ala Met Thr
225                 230                 235                 240
Ser Asn Val Ala Ser Val Gln Cys Asp Asn Ser Asp Lys Phe Pro Val
                245                 250                 255
Tyr Lys Tyr Pro Gly Lys Gly Cys Pro Thr Leu Gly Asp Glu Gly Asp
                260                 265                 270
Thr Asp Leu Tyr Asp Tyr Tyr Pro Glu Glu Asp Thr Glu Gly Asp Lys
            275                 280                 285
Val Arg Val Pro Arg Asp Cys Gly Cys Lys Pro Cys Ile Cys Thr Val
            290                 295                 300
Pro Glu Val Ser Ser Val Phe Ile Phe Pro Lys Pro Lys Asp Val
305                 310                 315                 320
Leu Thr Ile Thr Leu Thr Pro Lys Val Thr Cys Val Val Val Asp Ile
                325                 330                 335
Ser Lys Asp Asp Pro Glu Val Gln Phe Ser Trp Phe Val Asp Asp Val
            340                 345                 350
Glu Val His Thr Ala Gln Thr Gln Pro Arg Glu Glu Gln Phe Asn Ser
            355                 360                 365
Thr Phe Arg Ser Val Ser Glu Leu Pro Ile Met His Gln Asp Trp Leu
            370                 375                 380
Asn Gly Lys Glu Phe Lys Cys Arg Val Asn Ser Ala Ala Phe Pro Ala
385                 390                 395                 400
Pro Ile Glu Lys Thr Ile Ser Lys Thr Lys Gly Arg Pro Lys Ala Pro
                405                 410                 415
Gln Val Tyr Thr Ile Pro Pro Pro Lys Glu Gln Met Ala Lys Asp Lys
            420                 425                 430
Val Ser Leu Thr Cys Met Ile Thr Asp Phe Phe Pro Glu Asp Ile Thr
            435                 440                 445
Val Glu Trp Gln Trp Asn Gly Gln Pro Ala Glu Asn Tyr Lys Asn Thr
            450                 455                 460
Gln Pro Ile Met Asp Thr Asp Gly Ser Tyr Phe Val Tyr Ser Lys Leu
465                 470                 475                 480
Asn Val Gln Lys Ser Asn Trp Glu Ala Gly Asn Thr Phe Thr Cys Ser
                485                 490                 495
Val Leu His Glu Gly Leu His Asn His His Thr Glu Lys Ser Leu Ser
            500                 505                 510
```

His Ser Pro Gly Ile Gly His His His His His His
            515                 520                 525

<210> SEQ ID NO 33
<211> LENGTH: 526
<212> TYPE: PRT
<213> ORGANISM: Artificial Sequence
<220> FEATURE:
<223> OTHER INFORMATION: Synthetic

<400> SEQUENCE: 33

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Thr Val Asp Val Lys Ala Thr Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg Val Pro Arg Asp Cys Gly Cys Lys Pro Cys Ile Cys Thr Val
    290                 295                 300

Pro Glu Val Ser Ser Val Phe Ile Phe Pro Pro Lys Pro Lys Asp Val
305                 310                 315                 320

Leu Thr Ile Thr Leu Thr Pro Lys Val Thr Cys Val Val Val Asp Ile
                325                 330                 335

Ser Lys Asp Asp Pro Glu Val Gln Phe Ser Trp Phe Val Asp Asp Val
            340                 345                 350

-continued

Glu Val His Thr Ala Gln Thr Gln Pro Arg Glu Gln Phe Asn Ser
            355                 360                 365

Thr Phe Arg Ser Val Ser Glu Leu Pro Ile Met His Gln Asp Trp Leu
370                 375                 380

Asn Gly Lys Glu Phe Lys Cys Arg Val Asn Ser Ala Ala Phe Pro Ala
385                 390                 395                 400

Pro Ile Glu Lys Thr Ile Ser Lys Thr Lys Gly Arg Pro Lys Ala Pro
                405                 410                 415

Gln Val Tyr Thr Ile Pro Pro Lys Glu Gln Met Ala Lys Asp Lys
            420                 425                 430

Val Ser Leu Thr Cys Met Ile Thr Asp Phe Phe Pro Glu Asp Ile Thr
                435                 440                 445

Val Glu Trp Gln Trp Asn Gly Gln Pro Ala Glu Asn Tyr Lys Asn Thr
            450                 455                 460

Gln Pro Ile Met Asp Thr Asp Gly Ser Tyr Phe Val Tyr Ser Lys Leu
465                 470                 475                 480

Asn Val Gln Lys Ser Asn Trp Glu Ala Gly Asn Thr Phe Thr Cys Ser
                485                 490                 495

Val Leu His Glu Gly Leu His Asn His His Thr Glu Lys Ser Leu Ser
            500                 505                 510

His Ser Pro Gly Ile Gly His His His His His His
            515                 520                 525

<210> SEQ ID NO 34
<211> LENGTH: 526
<212> TYPE: PRT
<213> ORGANISM: Artificial Sequence
<220> FEATURE:
<223> OTHER INFORMATION: Synthetic

<400> SEQUENCE: 34

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
            195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Val Asp Val Lys Ala Val Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
                260                 265                 270

Thr Asp Leu Tyr Asp Tyr Pro Glu Glu Asp Thr Glu Gly Asp Lys
            275                 280                 285

Val Arg Val Pro Arg Asp Cys Gly Cys Lys Pro Cys Ile Cys Thr Val
            290                 295                 300

Pro Glu Val Ser Ser Val Phe Ile Phe Pro Lys Pro Lys Asp Val
305                 310                 315                 320

Leu Thr Ile Thr Leu Thr Pro Lys Val Thr Cys Val Val Asp Ile
                325                 330                 335

Ser Lys Asp Asp Pro Glu Val Gln Phe Ser Trp Phe Val Asp Asp Val
            340                 345                 350

Glu Val His Thr Ala Gln Thr Gln Pro Arg Glu Glu Gln Phe Asn Ser
                355                 360                 365

Thr Phe Arg Ser Val Ser Glu Leu Pro Ile Met His Gln Asp Trp Leu
    370                 375                 380

Asn Gly Lys Glu Phe Lys Cys Arg Val Asn Ser Ala Ala Phe Pro Ala
385                 390                 395                 400

Pro Ile Glu Lys Thr Ile Ser Lys Thr Lys Gly Arg Pro Lys Ala Pro
                405                 410                 415

Gln Val Tyr Thr Ile Pro Pro Lys Glu Gln Met Ala Lys Asp Lys
                420                 425                 430

Val Ser Leu Thr Cys Met Ile Thr Asp Phe Phe Pro Glu Asp Ile Thr
            435                 440                 445

Val Glu Trp Gln Trp Asn Gly Gln Pro Ala Glu Asn Tyr Lys Asn Thr
    450                 455                 460

Gln Pro Ile Met Asp Thr Asp Gly Ser Tyr Phe Val Tyr Ser Lys Leu
465                 470                 475                 480

Asn Val Gln Lys Ser Asn Trp Glu Ala Gly Asn Thr Phe Thr Cys Ser
                485                 490                 495

Val Leu His Glu Gly Leu His Asn His His Thr Glu Lys Ser Leu Ser
            500                 505                 510

His Ser Pro Gly Ile Gly His His His His His His
            515                 520                 525

<210> SEQ ID NO 35
<211> LENGTH: 296
<212> TYPE: PRT
<213> ORGANISM: Artificial Sequence
<220> FEATURE:
<223> OTHER INFORMATION: Synthetic

<400> SEQUENCE: 35

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

```
Thr Thr Ile Leu His Leu Ser Glu Asn Leu Leu Tyr Thr Phe Ser Leu
            35                  40                  45

Ala Thr Leu Met Pro Tyr Thr Arg Leu Thr Gln Leu Asn Leu Asp Arg
 50                  55                  60

Ser Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                 85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
            115                 120                 125

Leu Tyr Leu Lys Gly Asn Glu Leu Lys Thr Leu Pro Pro Gly Leu Leu
130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
            195                 200                 205

Cys Asn Cys Glu Ile Leu Tyr Phe Arg Arg Trp Leu Gln Asp Asn Ala
            210                 215                 220

Glu Asn Val Tyr Val Trp Lys Gln Val Val Asp Val Lys Ala Val Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
            275                 280                 285

Val Arg His His His His His
            290                 295

<210> SEQ ID NO 36
<211> LENGTH: 526
<212> TYPE: PRT
<213> ORGANISM: Artificial Sequence
<220> FEATURE:
<223> OTHER INFORMATION: Synthetic

<400> SEQUENCE: 36

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
            35                  40                  45

Ala Thr Leu Met Pro Tyr Thr Arg Leu Thr Gln Leu Asn Leu Asp Arg
 50                  55                  60

Ser Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                 85                  90                  95
```

```
Gln Thr Leu Pro Ala Leu Thr Val Leu Asp Val Ser Phe Asn Arg Leu
                100                 105                 110

Thr Ser Leu Pro Leu Gly Ala Leu Arg Gly Leu Gly Glu Leu Gln Glu
            115                 120                 125

Leu Tyr Leu Lys Gly Asn Glu Leu Lys Thr Leu Pro Pro Gly Leu Leu
        130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Gly Val Asp Val Lys Val Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg Val Pro Arg Asp Cys Gly Cys Lys Pro Cys Ile Cys Thr Val
    290                 295                 300

Pro Glu Val Ser Ser Val Phe Ile Phe Pro Pro Lys Pro Lys Asp Val
305                 310                 315                 320

Leu Thr Ile Thr Leu Thr Pro Lys Val Thr Cys Val Val Val Asp Ile
                325                 330                 335

Ser Lys Asp Asp Pro Glu Val Gln Phe Ser Trp Phe Val Asp Asp Val
            340                 345                 350

Glu Val His Thr Ala Gln Thr Gln Pro Arg Glu Glu Gln Phe Asn Ser
        355                 360                 365

Thr Phe Arg Ser Val Ser Glu Leu Pro Ile Met His Gln Asp Trp Leu
    370                 375                 380

Asn Gly Lys Glu Phe Lys Cys Arg Val Asn Ser Ala Ala Phe Pro Ala
385                 390                 395                 400

Pro Ile Glu Lys Thr Ile Ser Lys Thr Lys Gly Arg Pro Lys Ala Pro
                405                 410                 415

Gln Val Tyr Thr Ile Pro Pro Pro Lys Glu Gln Met Ala Lys Asp Lys
            420                 425                 430

Val Ser Leu Thr Cys Met Ile Thr Asp Phe Phe Pro Glu Asp Ile Thr
        435                 440                 445

Val Glu Trp Gln Trp Asn Gly Gln Pro Ala Glu Asn Tyr Lys Asn Thr
    450                 455                 460

Gln Pro Ile Met Asp Thr Asp Gly Ser Tyr Phe Val Tyr Ser Lys Leu
465                 470                 475                 480

Asn Val Gln Lys Ser Asn Trp Glu Ala Gly Asn Thr Phe Thr Cys Ser
                485                 490                 495

Val Leu His Glu Gly Leu His Asn His His Thr Glu Lys Ser Leu Ser
            500                 505                 510
```

His Ser Pro Gly Ile Gly His His His His His His
            515                 520                 525

<210> SEQ ID NO 37
<211> LENGTH: 526
<212> TYPE: PRT
<213> ORGANISM: Artificial Sequence
<220> FEATURE:
<223> OTHER INFORMATION: Synthetic

<400> SEQUENCE: 37

His Pro Ile Cys Glu Val Ser Lys Val Ala Ser His Leu Glu Val Asn
1               5                   10                  15

Cys Asp Lys Arg Asn Leu Thr Ala Leu Pro Asp Leu Pro Lys Asp
            20                  25                  30

Thr Thr Ile Leu His Leu Ser Glu Asn Leu Leu Tyr Thr Phe Ser Leu
            35                  40                  45

Ala Thr Leu Met Pro Tyr Thr Arg Leu Thr Gln Leu Asn Leu Asp Arg
        50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
210                 215                 220

Glu Asn Val Tyr Val Trp Lys Gln Gly Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg Val Pro Arg Asp Cys Gly Cys Lys Pro Cys Ile Cys Thr Val
290                 295                 300

Pro Glu Val Ser Ser Val Phe Ile Phe Pro Pro Lys Pro Lys Asp Val
305                 310                 315                 320

Leu Thr Ile Thr Leu Thr Pro Lys Val Thr Cys Val Val Val Asp Ile
                325                 330                 335

Ser Lys Asp Asp Pro Glu Val Gln Phe Ser Trp Phe Val Asp Asp Val
            340                 345                 350

Glu Val His Thr Ala Gln Thr Gln Pro Arg Glu Gln Phe Asn Ser
              355                 360                 365

Thr Phe Arg Ser Val Ser Glu Leu Pro Ile Met His Gln Asp Trp Leu
370                 375                 380

Asn Gly Lys Glu Phe Lys Cys Arg Val Asn Ser Ala Ala Phe Pro Ala
385                 390                 395                 400

Pro Ile Glu Lys Thr Ile Ser Lys Thr Lys Gly Arg Pro Lys Ala Pro
              405                 410                 415

Gln Val Tyr Thr Ile Pro Pro Lys Glu Gln Met Ala Lys Asp Lys
              420                 425                 430

Val Ser Leu Thr Cys Met Ile Thr Asp Phe Phe Pro Glu Asp Ile Thr
              435                 440                 445

Val Glu Trp Gln Trp Asn Gly Gln Pro Ala Glu Asn Tyr Lys Asn Thr
450                 455                 460

Gln Pro Ile Met Asp Thr Asp Gly Ser Tyr Phe Val Tyr Ser Lys Leu
465                 470                 475                 480

Asn Val Gln Lys Ser Asn Trp Glu Ala Gly Asn Thr Phe Thr Cys Ser
              485                 490                 495

Val Leu His Glu Gly Leu His Asn His His Thr Glu Lys Ser Leu Ser
              500                 505                 510

His Ser Pro Gly Ile Gly His His His His His His
              515                 520                 525

<210> SEQ ID NO 38
<211> LENGTH: 514
<212> TYPE: PRT
<213> ORGANISM: Artificial Sequence
<220> FEATURE:
<223> OTHER INFORMATION: Synthetic

<400> SEQUENCE: 38

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
              20                  25                  30

Thr Thr Ile Leu His Leu Ser Glu Asn Leu Leu Tyr Thr Phe Ser Leu
              35                  40                  45

Ala Thr Leu Met Pro Tyr Thr Arg Leu Thr Gln Leu Asn Leu Asp Arg
50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
              85                  90                  95

Gln Thr Leu Pro Ala Leu Thr Val Leu Asp Val Ser Phe Asn Arg Leu
              100                 105                 110

Thr Ser Leu Pro Leu Gly Ala Leu Arg Gly Leu Gly Glu Leu Gln Glu
              115                 120                 125

Leu Tyr Leu Lys Gly Asn Glu Leu Lys Thr Leu Pro Pro Gly Leu Leu
130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
              165                 170                 175

Leu Leu Leu Gln Glu Asn Ser Leu Tyr Thr Ile Pro Lys Gly Phe Phe
              180                 185                 190

Gly Ser His Leu Leu Pro Phe Ala Phe Leu His Gly Asn Pro Trp Leu
            195                 200                 205

Cys Asn Cys Glu Ile Leu Tyr Phe Arg Arg Trp Leu Gln Asp Asn Ala
        210                 215                 220

Glu Asn Val Tyr Ser Asn Val Ala Ser Val Gln Cys Asp Asn Ser Asp
225                 230                 235                 240

Lys Phe Pro Val Tyr Lys Tyr Pro Gly Lys Gly Cys Pro Thr Leu Gly
                245                 250                 255

Asp Glu Gly Asp Thr Asp Leu Tyr Asp Tyr Pro Glu Glu Asp Thr
            260                 265                 270

Glu Gly Asp Lys Val Arg Val Pro Arg Asp Cys Gly Cys Lys Pro Cys
            275                 280                 285

Ile Cys Thr Val Pro Glu Val Ser Ser Val Phe Ile Phe Pro Pro Lys
        290                 295                 300

Pro Lys Asp Val Leu Thr Ile Thr Leu Thr Pro Lys Val Thr Cys Val
305                 310                 315                 320

Val Val Asp Ile Ser Lys Asp Asp Pro Glu Val Gln Phe Ser Trp Phe
                325                 330                 335

Val Asp Asp Val Glu Val His Thr Ala Gln Thr Gln Pro Arg Glu Glu
            340                 345                 350

Gln Phe Asn Ser Thr Phe Arg Ser Val Ser Glu Leu Pro Ile Met His
            355                 360                 365

Gln Asp Trp Leu Asn Gly Lys Glu Phe Lys Cys Arg Val Asn Ser Ala
        370                 375                 380

Ala Phe Pro Ala Pro Ile Glu Lys Thr Ile Ser Lys Thr Lys Gly Arg
385                 390                 395                 400

Pro Lys Ala Pro Gln Val Tyr Thr Ile Pro Pro Lys Glu Gln Met
                405                 410                 415

Ala Lys Asp Lys Val Ser Leu Thr Cys Met Ile Thr Asp Phe Phe Pro
            420                 425                 430

Glu Asp Ile Thr Val Glu Trp Gln Trp Asn Gly Gln Pro Ala Glu Asn
            435                 440                 445

Tyr Lys Asn Thr Gln Pro Ile Met Asp Thr Asp Gly Ser Tyr Phe Val
450                 455                 460

Tyr Ser Lys Leu Asn Val Gln Lys Ser Asn Trp Glu Ala Gly Asn Thr
465                 470                 475                 480

Phe Thr Cys Ser Val Leu His Glu Gly Leu His Asn His His Thr Glu
                485                 490                 495

Lys Ser Leu Ser His Ser Pro Gly Ile Gly His His His His His
            500                 505                 510

His His

<210> SEQ ID NO 39
<211> LENGTH: 529
<212> TYPE: PRT
<213> ORGANISM: Artificial Sequence
<220> FEATURE:
<223> OTHER INFORMATION: Synthetic

<400> SEQUENCE: 39

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu

```
                35                  40                  45
Ala Thr Leu Met Pro Tyr Thr Arg Leu Thr Gln Leu Asn Leu Asp Arg
 50                  55                  60

Ser Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                 85                  90                  95

Gln Thr Leu Pro Ala Leu Thr Val Leu Asp Val Ser Phe Asn Arg Leu
                100                 105                 110

Thr Ser Leu Pro Leu Gly Ala Leu Arg Gly Leu Gly Glu Leu Gln Glu
                115                 120                 125

Leu Tyr Leu Lys Gly Asn Glu Leu Lys Thr Leu Pro Pro Gly Leu Leu
130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
                180                 185                 190

Gly Ser His Leu Leu Pro Phe Ala Phe Leu His Gly Asn Pro Trp Leu
                195                 200                 205

Cys Asn Cys Glu Ile Leu Tyr Phe Arg Arg Trp Leu Gln Asp Asn Ala
210                 215                 220

Glu Asn Val Tyr Val Trp Lys Gln Thr Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
                260                 265                 270

Thr Asp Leu Tyr Asp Tyr Tyr Pro Glu Glu Asp Thr Glu Gly Asp Lys
                275                 280                 285

Val Arg Pro Arg Gly Pro Thr Ile Lys Pro Cys Pro Pro Cys Lys Cys
290                 295                 300

Pro Ala Pro Asn Leu Leu Gly Gly Pro Ser Val Phe Ile Phe Pro Pro
305                 310                 315                 320

Lys Ile Lys Asp Val Leu Met Ile Ser Leu Ser Pro Ile Val Thr Cys
                325                 330                 335

Val Val Val Asp Val Ser Glu Asp Asp Pro Asp Val Gln Ile Ser Trp
                340                 345                 350

Phe Val Asn Asn Val Glu Val His Thr Ala Gln Thr Gln Thr His Arg
                355                 360                 365

Glu Asp Tyr Asn Ser Thr Leu Arg Val Val Ser Ala Leu Pro Ile Gln
                370                 375                 380

His Gln Asp Trp Met Ser Gly Lys Glu Phe Lys Cys Lys Val Asn Asn
385                 390                 395                 400

Lys Asp Leu Pro Ala Pro Ile Glu Arg Thr Ile Ser Lys Pro Lys Gly
                405                 410                 415

Ser Val Arg Ala Pro Gln Val Tyr Val Leu Pro Pro Glu Glu Glu
                420                 425                 430

Met Thr Lys Lys Gln Val Thr Leu Thr Cys Met Val Thr Asp Phe Met
                435                 440                 445

Pro Glu Asp Ile Tyr Val Glu Trp Thr Asn Asn Gly Lys Thr Glu Leu
450                 455                 460
```

```
Asn Tyr Lys Asn Thr Glu Pro Val Leu Asp Ser Asp Gly Ser Tyr Phe
465                 470                 475                 480

Met Tyr Ser Lys Leu Arg Val Glu Lys Lys Asn Trp Val Glu Arg Asn
                485                 490                 495

Ser Tyr Ser Cys Ser Val Val His Glu Gly Leu His Asn His His Thr
            500                 505                 510

Thr Lys Ser Phe Ser Arg Thr Pro Gly His His His His His His
        515                 520                 525

His

<210> SEQ ID NO 40
<211> LENGTH: 323
<212> TYPE: PRT
<213> ORGANISM: Artificial Sequence
<220> FEATURE:
<223> OTHER INFORMATION: Synthetic

<400> SEQUENCE: 40

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Thr Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Pro Glu Glu Asp Thr Glu Gly Asp Lys
        275                 280                 285
```

```
Val Arg Gly Tyr Ile Pro Glu Ala Pro Arg Asp Gly Gln Ala Tyr Val
    290                 295                 300

Arg Lys Asp Gly Glu Trp Val Leu Leu Ser Thr Phe Leu His His His
305                 310                 315                 320

His His His

<210> SEQ ID NO 41
<211> LENGTH: 390
<212> TYPE: PRT
<213> ORGANISM: Artificial Sequence
<220> FEATURE:
<223> OTHER INFORMATION: Synthetic

<400> SEQUENCE: 41

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
                20                  25                  30

Thr Thr Ile Leu His Leu Ser Glu Asn Leu Leu Tyr Thr Phe Ser Leu
            35                  40                  45

Ala Thr Leu Met Pro Tyr Thr Arg Leu Thr Gln Leu Asn Leu Asp Arg
50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
210                 215                 220

Glu Asn Val Tyr Val Trp Lys Gln Thr Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg Gly Ser His Met Trp Lys Gln Ser Val Glu Leu Ala Lys Lys
290                 295                 300

Asp Ser Leu Tyr Lys Asp Ala Met Gln Tyr Ala Ser Glu Ser Lys Asp
305                 310                 315                 320

Thr Glu Leu Ala Glu Glu Leu Leu Gln Trp Phe Leu Gln Glu Glu Lys
```

```
                    325                 330                 335
Arg Glu Cys Phe Gly Ala Cys Leu Phe Thr Cys Tyr Asp Leu Leu Arg
                340                 345                 350

Pro Asp Val Val Leu Glu Leu Ala Trp Arg His Asn Ile Met Asp Phe
            355                 360                 365

Ala Met Pro Tyr Phe Ile Gln Val Met Lys Glu Tyr Leu Thr Lys Val
        370                 375                 380

His His His His His His
385                 390

<210> SEQ ID NO 42
<211> LENGTH: 290
<212> TYPE: PRT
<213> ORGANISM: Artificial Sequence
<220> FEATURE:
<223> OTHER INFORMATION: Synthetic

<400> SEQUENCE: 42

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Ala Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Val Val Asp Val Lys Ala Val Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg
```

290

<210> SEQ ID NO 43
<211> LENGTH: 8
<212> TYPE: PRT
<213> ORGANISM: Artificial Sequence
<220> FEATURE:
<223> OTHER INFORMATION: Synthetic

<400> SEQUENCE: 43

His His His His His His His His
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic

<400> SEQUENCE: 44

Gly His His His His His His His His
1               5

<210> SEQ ID NO 45
<211> LENGTH: 27
<212> TYPE: PRT
<213> ORGANISM: Artificial Sequence
<220> FEATURE:
<223> OTHER INFORMATION: Synthetic

<400> SEQUENCE: 45

Glu Glu Asp Thr Glu Asp Tyr Lys Asp His Asp Gly Asp Tyr Lys Asp
1               5                   10                  15

His Asp Ile Asp Tyr Lys Asp Asp Asp Lys
            20                  25

<210> SEQ ID NO 46
<211> LENGTH: 236
<212> TYPE: PRT
<213> ORGANISM: Artificial Sequence
<220> FEATURE:
<223> OTHER INFORMATION: Synthetic

<400> SEQUENCE: 46

Val Pro Arg Asp Cys Gly Cys Lys Pro Cys Ile Cys Thr Val Pro Glu
1               5                   10                  15

Val Ser Ser Val Phe Ile Phe Pro Pro Lys Pro Lys Asp Val Leu Thr
            20                  25                  30

Ile Thr Leu Thr Pro Lys Val Thr Cys Val Val Val Asp Ile Ser Lys
        35                  40                  45

Asp Asp Pro Glu Val Gln Phe Ser Trp Phe Val Asp Asp Val Glu Val
    50                  55                  60

His Thr Ala Gln Thr Gln Pro Arg Glu Glu Gln Phe Asn Ser Thr Phe
65                  70                  75                  80

Arg Ser Val Ser Glu Leu Pro Ile Met His Gln Asp Trp Leu Asn Gly
                85                  90                  95

Lys Glu Phe Lys Cys Arg Val Asn Ser Ala Ala Phe Pro Ala Pro Ile
            100                 105                 110

Glu Lys Thr Ile Ser Lys Thr Lys Gly Arg Pro Lys Ala Pro Gln Val
        115                 120                 125

Tyr Thr Ile Pro Pro Pro Lys Glu Gln Met Ala Lys Asp Lys Val Ser

```
                    130                 135                 140
Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Asp Thr Asp Gly Ser Tyr Phe Val Tyr Ser Lys Leu Asn Val
            180                 185                 190

Gln Lys Ser Asn Trp Glu Ala Gly Asn Thr Phe Thr Cys Ser Val Leu
        195                 200                 205

His Glu Gly Leu His Asn His His Thr Glu Lys Ser Leu Ser His Ser
        210                 215                 220

Pro Gly Ile Gly His His His His His His
225             230                 235
```

COMPOSITION COMPRISING RECOMBINANT GPLBα RECEPTOR PROTEIN

SEQUENCE LISTING

Applicant incorporates by reference a CRF sequence listing having file name "GRDD0005PA_ST25.txt" (113 kB), created Aug. 18, 2021.

BACKGROUND von Willebrand Disease (vWD) is a common, heritable, mild bleeding disorder known to pose significant diagnostic challenges. Patients with vWD may not suffer from bleeding during their daily life, but during periods of hemostatic challenge (e.g., dental work, surgery, childbirth, or transfusion) problems may occur. Prior to hemostatically-challenging procedures, physicians routinely order a hemostasis panel, which often leads to additional tests specific to vWD.

von Willebrand Factor (vWF) binds to many different extracellular and cell-surface molecules and plays an important role in hemostasis and coagulation. vWF is particularly important in the formation of a platelet plug, and it specifically binds a number of platelet cell-surface protein complexes including the glycoprotein Ibα-V-IX complex, which crosslinks platelets and other extracellular molecules (e.g., subendothelial collagen). The glycoprotein Ibα-V-IX complex is composed by four subunits, GPIbα, GPIbβ, GPV and GPIX, and is present in the membrane of platelets. GPIbα and GPIbβ are linked by disulfide bridges, while the GPV and GPIX associate non-covalently with the complex. GPIbα subunit bears the binding site for vWF, α-thrombin, leukocyte integrin αMβ2 and β-selectin.

vWD diagnosis is complicated by its various types, which traditionally require multiple tests to provide a clear understanding of the underlying disease mechanism. Type 1 vWD is caused by a quantitative deficiency of vWF. Type 2 vWD is caused by a qualitative vWF deficiency. Type 2 vWD is further subdivided into type 2A, caused by mutations that decrease the proportion of functional vWF multimers, which decreases platelet adhesion; type 2B, caused by mutations to vWF that increase platelet-vWF binding; type 2M, caused by mutations that decrease vWF-dependent platelet adhesion; and type 2N, caused by mutations that impair binding to factor VIII. Type 3 vWD is caused by a virtually complete deficiency of vWF and decreased factor VIII, which is normally stabilized by circulating vWF. Acquired vWD is a relatively rare acquired bleeding disorder that usually occurs in elderly patients, in association with another underlying pathology. Finally, platelet-type vWD results from enhanced binding of vWF to glycoprotein Ibα (GPIbα), caused by mutation of the gene encoding GPIbα. Different assays have been developed to quantify vWF activity, such as the vWF antigen assay (vWF:Ag), which measures the total concentration of vWF in plasma, or the ristocetin cofactor assay (vWF:RCo) which measures binding of vWF to GPIbα of platelets during agglutination induced by the antibiotic ristocetin. However, vWF:Ag assay only provides information about quantitative level of vWF present in a patient's plasma without concerning the quality of the VWF present. Thus, the VWF:Ag on its own will not permit detection of many qualitative defects. In turn, the vWF:RCo assay can suffer from imprecision due to interference from bilirubin, hemoglobin, human anti-mouse antibodies (HAMA) rheumatoid factor, and triglycerides.

Further adding to the imprecision of the assay is the genetic variance and polymorphisms at the Ristocetin binding site. The accuracy of the vWF:RCo is especially low with decreased vVWF:Ag concentrations.

Said assays rely upon the binding of vWF to the extracellular domain of glycoprotein Ibα. In the absence of the glycoprotein Ibα-V-IX complex and shear stress, however, vWF binds to glycoprotein Ibα with relatively weak 4.5 µM affinity. Naturally-occurring mutations to glycoprotein Ibα identified in patients with platelet-type vWD include W230L, G233V, G233S, D235Y, M239V, and M239I, each of which increase the binding affinity between vWF and glycoprotein Ibα [1] to [9].

Due to the complexity of vWD, no single laboratory test is capable of providing a complete diagnosis. Diagnosis of vWD is currently under-reported such that the World Health Organization reports its prevalence at 1.14 in 100,000 while diagnostic studies report the prevalence at ~1% of the general population. A variety of tests are available for diagnosis, but expert opinion is often heavily-weighted. Accurate tests and clearly-defined diagnostic criteria could improve medical outcomes for many patients whose disease remains undiagnosed.

The inventors of the present invention have identified novel mutations in the Gp1bα β-hairpin that improve binding to vWF A1 domain. The inventors have also developed new recombinant polypeptides comprising said mutations to be used in the diagnosis of vWD.

SUMMARY

Various aspects of the embodiments relate to a recombinant polypeptide that specifically binds human von Willebrand Factor. A recombinant polypeptide typically includes a modified extracellular domain of platelet glycoprotein Ibα, which typically comprises at least one mutation selected from G233T, D235V, and K237V, relative to SEQ ID NO: 19. A recombinant polypeptide typically lacks a transmembrane domain.

In some embodiments, the recombinant polypeptide has a higher binding affinity for the von Willebrand Factor of a human blood sample or human blood plasma sample than a control polypeptide that does not comprise the at least one mutation but that is otherwise identical to the recombinant polypeptide.

In some embodiments, the Kd of the recombinant polypeptide and human von Willebrand Factor is less than 1 µM, 750 nM, 500 nM, 250 nM, or 100 nM. Kd may be determined, for example, by fluorescence anisotropy or surface plasmon resonance, although the method to determine Kd is not particularly limiting. Fluorescence anisotropy analysis may be performed, for example, on fluorescently-labelled von Willebrand Factor and recombinant polypeptide bound to slow-tumbling particles. Surface plasmon resonance may be performed, for example, on surface-bound von Willebrand Factor and soluble recombinant polypeptide.

In some embodiments, the modified extracellular domain comprises mutations C65S and G233T; mutations C65S and D235V; mutations C65S and K237V; or mutations C65S, G233T, and M239T, relative to SEQ ID NO: 19.

In some embodiments, a modified extracellular domain has at least about 95% sequence identity with at least about 250 consecutive amino acids of the amino acid sequence set forth in SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; or SEQ ID NO: 9. For example, a modified extracellular domain can optionally comprise the amino acid sequence set forth in SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; or SEQ ID NO: 9.

In some embodiments, a modified extracellular domain has at least about 95% sequence identity with at least about 250 consecutive amino acids of the amino acid sequence set forth in SEQ ID NO: 2; SEQ ID NO: 3; SEQ ID NO:4; or SEQ ID NO: 5. For example, a modified extracellular domain can optionally comprise the amino acid sequence set forth in SEQ ID NO: 2; SEQ ID NO: 3; SEQ ID NO: 4; or SEQ ID NO: 5.

In some embodiments, a recombinant polypeptide further comprises a cross-linking domain. A cross-linking domain optionally comprises one or more of a C-terminal cysteine, a negatively-charged C-terminal domain, and streptavidin binding protein. In some embodiments, the amino acid sequence of the cross-linking domain is selected from the group consisting SEQ ID NO: 11; SEQ ID NO: 12; SEQ ID NO: 16; SEQ ID NO: 17; or SEQ ID NO: 18.

In some embodiments, a recombinant polypeptide further comprises an affinity tag. An affinity tag may optionally be selected from polyhistidine tag, Snap tag, Clip tag, HaloTag, SnoopTag, SpyTag, chitin binding protein, maltose binding protein, Strep-tag, glutathione-S-transferase, FLAG-tag, V5-tag, Myc-tag, HA-tag, NE-tag, AviTag, Calmodulin-tag, polyglutamate, S-tag, SBP-tag, Softag 1, Softag 3, TC tag, VSV-tag, Xpress tag, Isopeptag, biotin carboxyl carrier protein, green fluorescent protein-tag, Nus-tag, thioredoxin-tag and the Fc domain of an antibody, although the choice of the affinity tag is not particularly limiting. In some embodiments the affinity tag is a polyhistidine tag comprising between 6 and 8 histidine residues. In some embodiments, the amino acid sequence of the affinity tag is selected from the group consisting of SEQ ID NO: 11; SEQ ID NO: 12; SEQ ID NO: 15; SEQ ID NO: 16; SEQ ID NO: 17; SEQ ID NO: 18; SEQ ID NO: 43, SEQ ID NO: 44; SEQ ID NO: 45; or SEQ ID NO: 46.

In some embodiments, a recombinant polypeptide further comprises an oligomerization domain. An oligomerization domain may be capable of forming a dimer, trimer, tetramer, or pentamer such as a homo-dimer, homo-trimer, homo-tetramer, or homo-pentamer. The oligomerization domain may be derived from p53, GCN4, clathrin, pent-tag, or the Fc domain of an antibody. In some embodiments, the oligomerization domain is selected from the group consisting of p53, GCN4, clathrin, pent-tag, or the Fc domain of an antibody. In some embodiments, the amino acid sequence of the oligomerization domain is selected from the group consisting of SEQ ID NO: 10; SEQ ID NO: 11; SEQ ID NO: 12; SEQ ID NO: 13; SEQ ID NO: 14; or SEQ ID NO: 46

In some embodiments, the amino acid sequence of the recombinant polypeptide has at least about 95% sequence identity with the amino acid sequence set forth in SEQ ID NO: 21; SEQ ID NO: 22; SEQ ID NO: 24; SEQ ID NO: 25; SEQ ID NO: 30; SEQ ID NO: 31; SEQ ID NO: 33; SEQ ID NO: 39; SEQ ID NO: 40; or SEQ ID NO: 41. In some embodiments the amino acid sequence of the recombinant polypeptide is selected from the group consisting of SEQ ID NO: 21; SEQ ID NO: 22; SEQ ID NO: 24; SEQ ID NO: 25; SEQ ID NO: 30; SEQ ID NO: 31; SEQ ID NO: 33; SEQ ID NO: 39; SEQ ID NO: 40; or SEQ ID NO: 41.

Various aspect of the embodiments relate to a recombinant polypeptide that specifically binds human von Willebrand Factor, comprising a modified extracellular domain of platelet glycoprotein Ibα, wherein the modified extracellular domain comprises mutations C65A, G233V and M239V, relative to SEQ ID NO: 19. In some embodiments, the amino acid sequence of the modified extracellular domain comprises the amino acid sequence set forth in of SEQ ID NO: 42. In some embodiments the amino acid sequence of the recombinant polypeptide is selected from the group consisting of SEQ ID NO: 26; SEQ ID NO: 27; or SEQ ID NO: 28.

In some embodiments, the recombinant polypeptide has a higher binding affinity for the von Willebrand Factor of a human blood sample or human blood plasma sample than a control polypeptide that does not comprise the mutations C65A, G233V and M239V, relative to SEQ ID NO: 19, but that is otherwise identical to the recombinant polypeptide.

In some embodiments, a recombinant polypeptide further comprises a cross-linking domain. A cross-linking domain optionally comprises one or more of a C-terminal cysteine, a negatively-charged C-terminal domain, and streptavidin binding protein. In some embodiments, the amino acid sequence of the cross-linking domain is selected from the group consisting SEQ ID NO: 11; SEQ ID NO: 12; SEQ ID NO: 16; SEQ ID NO: 17; or SEQ ID NO: 18.

In some embodiments, a recombinant polypeptide further comprises an affinity tag. An affinity tag may optionally be selected from polyhistidine tag, Snap tag, Clip tag, HaloTag, SnoopTag, SpyTag, chitin binding protein, maltose binding protein, Strep-tag, glutathione-S-transferase, FLAG-tag, V5-tag, Myc-tag, HA-tag, NE-tag, AviTag, Calmodulin-tag, polyglutamate, S-tag, SBP-tag, Softag 1, Softag 3, TC tag, VSV-tag, Xpress tag, Isopeptag, biotin carboxyl carrier protein, green fluorescent protein-tag, Nus-tag, thioredoxin-tag and the Fc domain of an antibody, although the choice of the affinity tag is not particularly limiting. In some embodiments the affinity tag is a polyhistidine tag comprising between 6 and 8 histidine residues. In some embodiments, the amino acid sequence of the affinity tag is selected from the group consisting of SEQ ID NO: 11; SEQ ID NO: 12; SEQ ID NO: 15; SEQ ID NO: 16; SEQ ID NO: 17; SEQ ID NO: 18; SEQ ID NO: 43, SEQ ID NO: 44; SEQ ID NO: 45; or SEQ ID NO: 46.

In some embodiments, a recombinant polypeptide further comprises an oligomerization domain. An oligomerization domain may be capable of forming a dimer, trimer, tetramer, or pentamer such as a homo-dimer, homo-trimer, homo-tetramer, or homo-pentamer. The oligomerization domain may be derived from p53, GCN4, clathrin, pent-tag, or the Fc domain of an antibody. In some embodiments, the the oligomerization domain is selected from the group consisting of p53, GCN4, clathrin, pent-tag, or the Fc domain of an antibody. In some embodiments, the amino acid sequence of the oligomerization domain is selected from the group consisting of SEQ ID NO: 10; SEQ ID NO: 11; SEQ ID NO: 12; SEQ ID NO: 13; SEQ ID NO: 14; or SEQ ID NO: 46

Various aspects of the embodiments relate to a recombinant polypeptide that specifically binds human von Willebrand Factor, comprising a modified extracellular domain of platelet glycoprotein Ibα, wherein the modified extracellular domain comprises the A238V mutation, relative to SEQ ID NO: 19. Such recombinant polypeptides typically have a lower binding affinity for von Willebrand Factor of a human blood or a human blood plasma sample than a control polypeptide that does not comprise the A238V mutation but that is otherwise identical to the recombinant polypeptide. In some embodiments, the amino acid sequence of the modified extracellular domain comprises the amino acid sequence set forth in of SEQ ID NO: 6. In some embodiments, the amino acid sequence of the recombinant polypeptide is SEQ ID NO: 36.

Various aspects of the embodiments relate to a recombinant polypeptide that specifically binds human von Willebrand Factor, comprising a modified extracellular domain of platelet glycoprotein Ibα, wherein the modified extracellular domain comprises the Δ(229-240) mutation, relative to SEQ ID NO: 19. Such recombinant polypeptides typically have a lower binding affinity for von Willebrand Factor of a human blood or a human blood plasma sample than a control polypeptide that does not comprise the Δ(229-240) mutation but that is otherwise identical to the recombinant polypeptide.

In some embodiments, the amino acid sequence of the modified extracellular domain comprises the amino acid sequence set forth in of SEQ ID NO: 9. In some embodiments, the amino acid sequence of the recombinant polypeptide is SEQ ID NO: 38.

Various aspects of the embodiments relate to a recombinant polypeptide that specifically binds human von Willebrand Factor, comprising a modified extracellular domain of platelet glycoprotein Ibα, wherein the modified extracellular domain comprises the A238V mutation or the Δ(229-240) mutation, relative to SEQ ID NO: 19. Such recombinant polypeptides typically have a lower binding affinity for von Willebrand Factor of a human blood or a human blood plasma sample than a control polypeptide that does not comprise the A238V mutation or the Δ(229-240) mutation but that is otherwise identical to the recombinant polypeptide.

In some embodiments, the amino acid sequence of the modified extracellular domain comprises the amino acid sequence set forth in of SEQ ID NO: 6 or SEQ ID NO: 9. In some embodiments, the amino acid sequence of the recombinant polypeptide is SEQ ID NO: 36 or SEQ ID NO: 38.

In some embodiments, a recombinant polypeptide further comprises a cross-linking domain. A cross-linking domain optionally comprises one or more of a C-terminal cysteine, a negatively-charged C-terminal domain, and streptavidin binding protein. In some embodiments, the amino acid sequence of the cross-linking domain is selected from the group consisting SEQ ID NO: 11; SEQ ID NO: 12; SEQ ID NO: 16; SEQ ID NO: 17; or SEQ ID NO: 18.

In some embodiments, a recombinant polypeptide further comprises an affinity tag. An affinity tag may optionally be selected from polyhistidine tag, Snap tag, Clip tag, HaloTag, SnoopTag, SpyTag, chitin binding protein, maltose binding protein, Strep-tag, glutathione-S-transferase, FLAG-tag, V5-tag, Myc-tag, HA-tag, NE-tag, AviTag, Calmodulin-tag, polyglutamate, S-tag, SBP-tag, Softag 1, Softag 3, TC tag, VSV-tag, Xpress tag, Isopeptag, biotin carboxyl carrier protein, green fluorescent protein-tag, Nus-tag, thioredoxin-tag and the Fc domain of an antibody, although the choice of the affinity tag is not particularly limiting. In some embodiments the affinity tag is a polyhistidine tag comprising between 6 and 8 histidine residues. In some embodiments, the amino acid sequence of the affinity tag is selected from the group consisting of SEQ ID NO: 11; SEQ ID NO: 12; SEQ ID NO: 15; SEQ ID NO: 16; SEQ ID NO: 17; SEQ ID NO: 18; SEQ ID NO: 43, SEQ ID NO: 44; SEQ ID NO: 45; or SEQ ID NO: 46.

In some embodiments, a recombinant polypeptide further comprises an oligomerization domain. An oligomerization domain may be capable of forming a dimer, trimer, tetramer, or pentamer such as a homo-dimer, homo-trimer, homo-tetramer, or homo-pentamer. The oligomerization domain may be derived from p53, GCN4, clathrin, pent-tag, or the Fc domain of an antibody. In some embodiments, the the oligomerization domain is selected from the group consisting of p53, GCN4, clathrin, pent-tag, or the Fc domain of an antibody. In some embodiments, the amino acid sequence of the oligomerization domain is selected from the group consisting of SEQ ID NO: 10; SEQ ID NO: 11; SEQ ID NO: 12; SEQ ID NO: 13; SEQ ID NO: 14; or SEQ ID NO: 46

In some embodiments, the recombinant polypeptide further comprises a leader peptide. In some embodiments, the amino acid sequence of the leader peptide is SEQ ID NO: 20.

In some embodiments the amino acid sequence of the recombinant polypeptide is selected from the group consisting of SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; or SEQ ID NO: 41.

Various aspects of the invention relate to an oligomeric polypeptide comprising at least two of the recombinant polypeptides described herein.

Various aspects of the invention relate to a cell comprising a recombinant polypeptide or oligomeric polypeptide described herein. The cell can optionally be selected from a CHO, HEK, BHK, NS0, Sp2/0, COS, C127, HT-1080, PER.C6, HeLa, or Jurkat cell.

Various aspects of the invention relate to a nucleic acid comprising a nucleotide sequence encoding a recombinant polypeptide described herein. The nucleic acid typically also comprises a promoter that is operably linked to the nucleotide sequence encoding the recombinant polypeptide (e.g., so that the promoter can drive transcription of the nucleotide sequence in an appropriate expression cell).

Various aspects of the invention relate to a cell comprising a nucleic acid described herein (e.g., supra). The cell may be an expression cell (e.g., a CHO, HEK, BHK, NS0, Sp2/0, COS, C127, HT-1080, PER.C6, HeLa, or Jurkat cell) or a cloning cell (e.g., *E. coli*).

Various aspects of the invention relate to a composition comprising a recombinant polypeptide or oligomeric polypeptide described herein and a solid support, wherein the recombinant polypeptide or oligomeric polypeptide is (a) covalently or non-covalently bound to the solid support and/or (b) directly or indirectly bound to the solid support.

The solid support may optionally either be or comprise a particle, a bead, a membrane, a surface, a polypeptide chip, a microtiter plate, or the solid-phase of a chromatography column. For example, in some embodiments, the solid support is a latex particle.

In some embodiments, a composition further comprises von Willebrand Factor (such as human von Willebrand Factor).

In some embodiments, a composition comprises a solid support comprising a plurality of particles or beads, and von Willebrand Factor cross-links the particles or beads of the plurality of particles or beads.

In some embodiments, a composition further comprises blood plasma (such as human blood plasma).

In some embodiments, a composition further comprises platelets (such as human platelets).

BRIEF DESCRIPTION OF THE DRAWINGS

FIG. 1 contains photographs of sodium dodecyl sulfate polyacrylamide gel electrophoresis (SDS-PAGE) gels that confirm the expression and purity of various recombinant polypeptides. The lanes of the gels are numbered as follows: (1) molecular weight standard; (2) recombinant polypeptide comprising the C65S and G233T mutations, IgG1 Fc dimerization domain, and 8-His affinity tag (arrowhead; the lower band corresponds to the murine IgG1 constant domain) (SEQ ID NO: 21); (3) recombinant polypeptide comprising the C65S and G233T mutations, p53 tetramerization domain, and 6-His affinity tag (SEQ ID NO: 22); (4) recombinant polypeptide comprising the C65S, G233V, and M239V mutations, p53 tetramerization domain, and 6-His affinity tag (SEQ ID NO: 23); (5) recombinant polypeptide comprising the C65S and G233T mutations, 6-His affinity tag, and C-terminal cysteine (SEQ ID NO: 24); (6) recombinant polypeptide comprising the C65S and G233T mutations, streptavidin binding protein, and 6-His affinity tag (SEQ ID NO: 25); (7) recombinant polypeptide comprising the C65A, G233V, and M239V mutations, p53 tetramerization domain, and 6-His affinity tag (SEQ ID NO: 26); (8) molecular weight standard; (9) molecular weight standard; (10) recombinant polypeptide comprising the C65A, G233V, and M239V mutations and 6-His affinity tag (SEQ ID NO: 27); (11) recombinant polypeptide comprising the C65A, G233V, and M239V mutations, negatively-charged C-terminal domain, and 6-His affinity tag (SEQ ID NO: 28); (12) recombinant polypeptide comprising the G233V and M239V mutations, FLAG tag and 6-His affinity tag (SEQ ID NO: 29).

Figure 2:
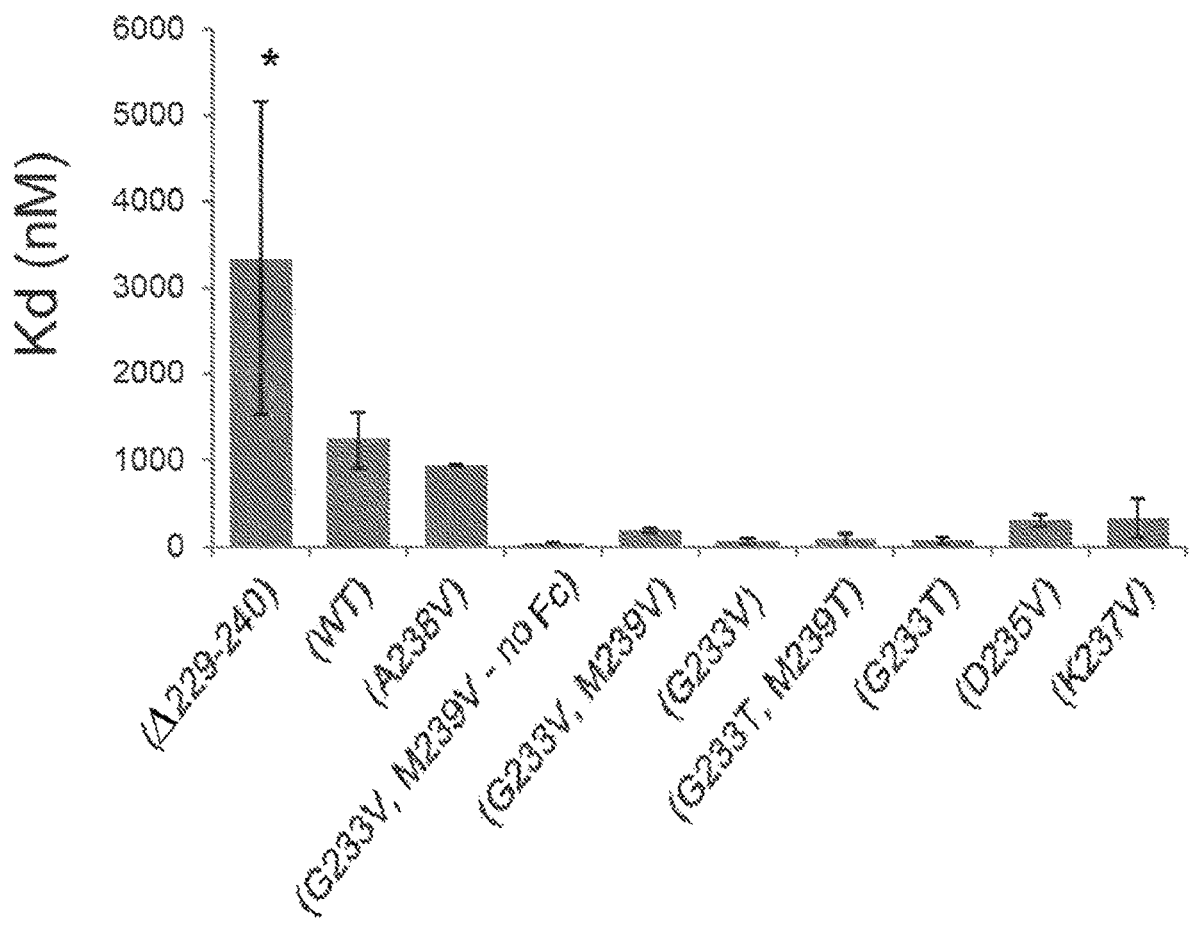

FIG. 2 is a bar graph depicting dissociation constants (Kd; y-axis) as assessed by fluorescence anisotropy between fluorescently-labelled recombinant von Willebrand Factor A1 domain and particle-bound dimeric polypeptides comprising two recombinant polypeptide subunits each comprising an Fc dimerization domain and a modified extracellular domain of platelet glycoprotein Ibα, which include mutations as indicated on the x-axis and C65S mutation, or a particle-bound monomeric polypeptide control (G233V, M239V-noFc (SEQ ID NO: 35)). The dimeric polypeptides assessed correspond to SEQ ID NO: 38 (Δ(229-240)); SEQ ID NO: 37 (WT); SEQ ID NO: 36 (A238V); SEQ ID NO: 34 (G233V, M239V); SEQ ID NO: 32 (G233V); SEQ ID NO: 33 (G233T, M239T); SEQ ID NO: 21 (G233T); SEQ ID NO: 30 (D235V); SEQ ID NO: 31 (K237V). Dimeric polypeptide that did not include a mutation displayed a Kd of about 1.25 μM. Recombinant polypeptides that included one of the G233T, D235V, or K237V mutations each displayed Kds less than 500 nM (e.g., ~67 nM, ~250 nM, and ~300 nM, respectively, for single mutants).

Figure 3:
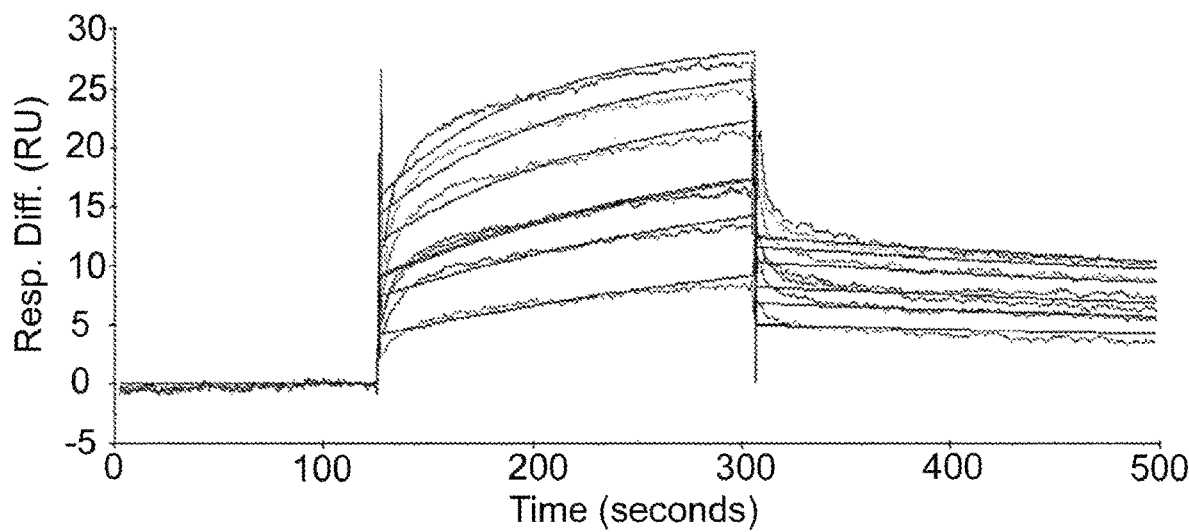

FIG. 3 is a line graph of a Biacore surface plasmon resonance analysis of surface-bound von Willebrand factor and soluble recombinant polypeptide comprising a modified extracellular domain of platelet glycoprotein Ibα that includes the G233T mutation. This analysis suggests that the dissociation constant (Kd) between the von Willebrand Factor and G233T recombinant polypeptide was 58 nM, which confirms the fluorescence anisotropy Kd measurements of FIG. 2, which measured a Kd of 67 nM for the G233T mutant.

Figure 4A:
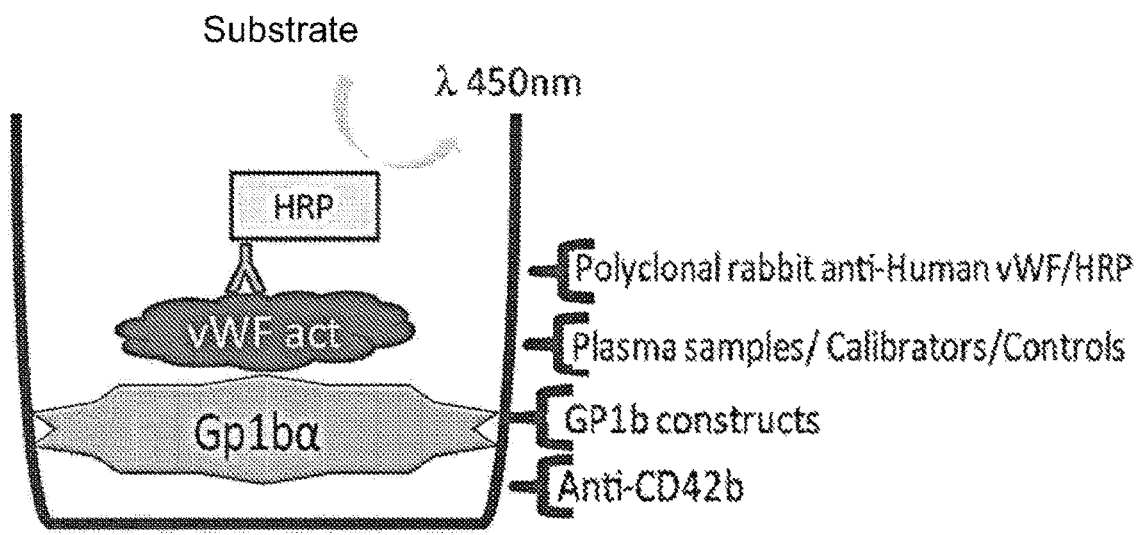
Figure 4B:
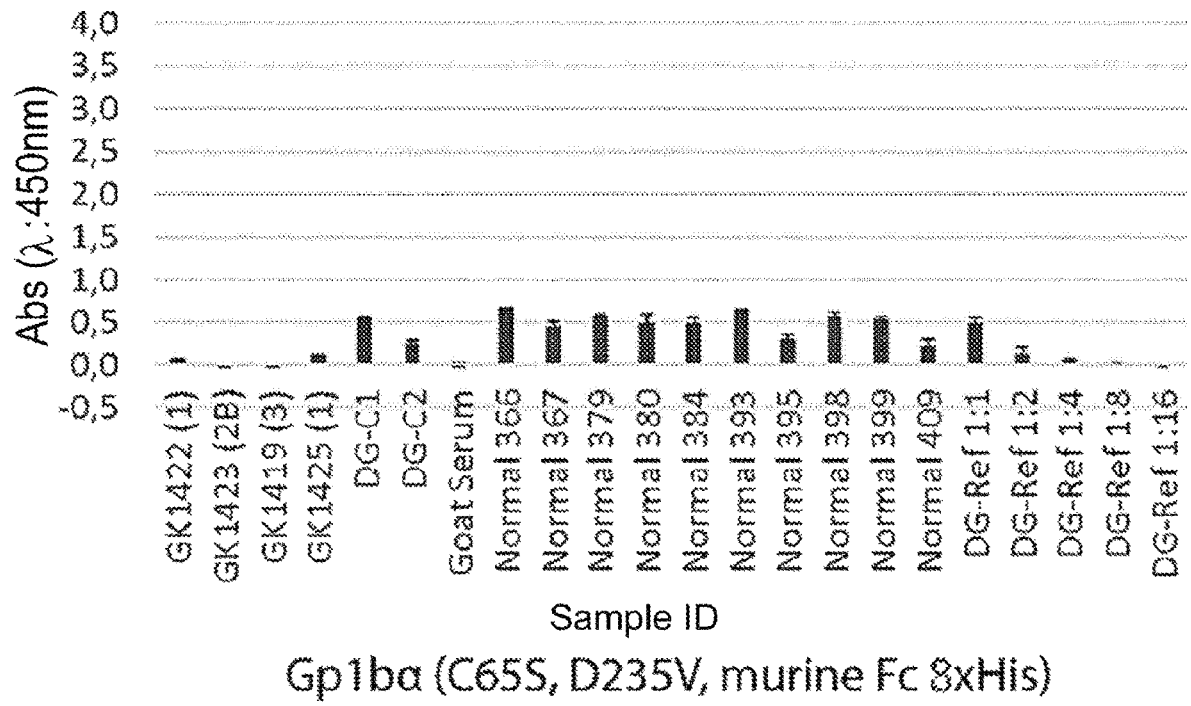
Figure 4C:
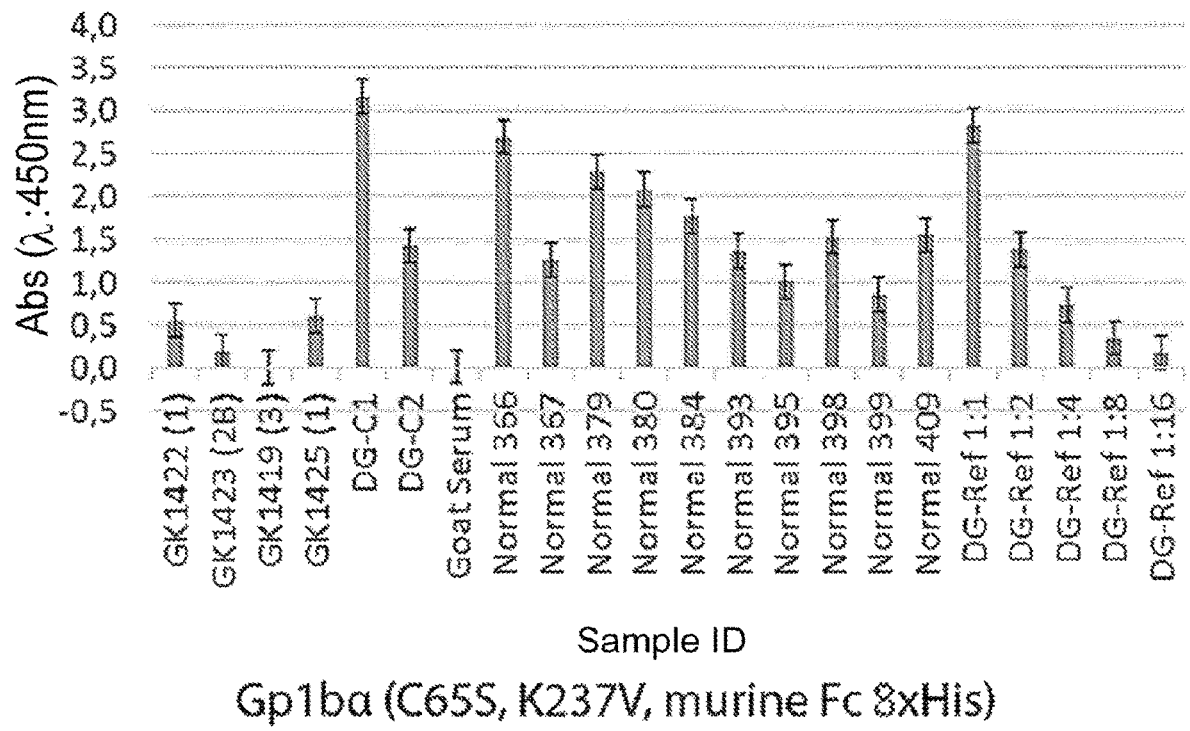
Figure 4D:
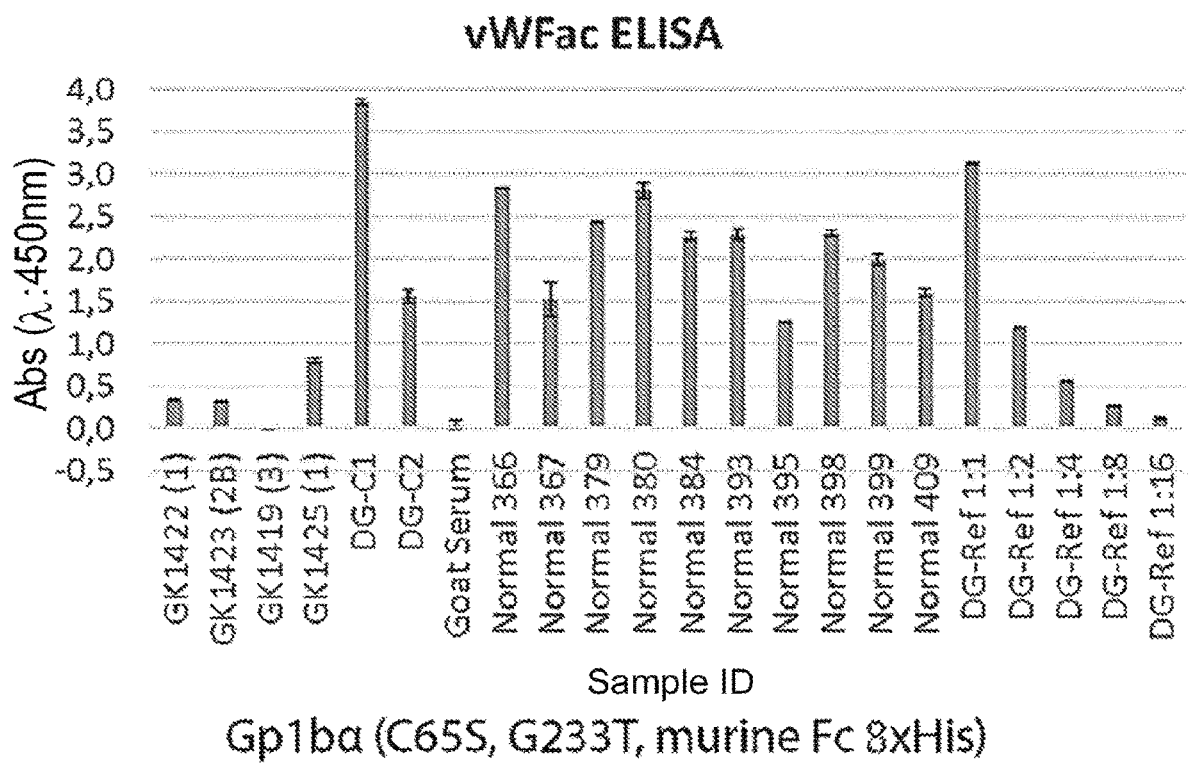

FIG. 4A is a cartoon of the enzyme-linked immunosorbent assay (ELISA) used to generate the data in FIG. 4B-4D. A solid support was coated with anti-glycoprotein Ibα antibody (anti-CD42b), which was used to immobilize recombinant polypeptide comprising a modified extracellular domain of platelet glycoprotein Ibα (CD42b; GPIbα; GP1b constructs). The solid support was then contacted with human blood plasma, von Willebrand Factor calibrators, or von Willebrand Factor controls. The solid support was then contacted with a polyclonal rabbit anti-human von Willebrand Factor antibody to which horseradish peroxidase (HRP) was conjugated. The composition was then contacted with a substrate capable of being converted into a product by HRP with a strong absorbance at 450 nm, and absorbance was measured.

FIG. 4B is a bar graph depicting results for the ELISA of FIG. 4A using recombinant polypeptide comprising a modified extracellular domain of platelet glycoprotein Ibα including the C65S and D235V mutations (SEQ ID NO: 30). The first four samples on the x-axis correspond to samples with known type 1, type 2B, type 3, and type 1 von Willebrand Disease, respectively (i.e., GK1422 (1); GH1423 (2B); GK1419 (3); GK1425 (1)). The fifth and sixth samples are control samples comprising pooled human plasma (i.e., DG-C1; DG-C2). The seventh sample is a goat blood serum control (which lacks von Willebrand Factor). The eighth through seventeenth samples are human blood plasma samples without von Willebrand Disease ("normal"). The eighteenth to twenty-second samples correspond to a serial dilution of a reference standard of pooled human plasma from no dilution (1:1) to 16-fold dilution (1:16). The y-axis corresponds to absorbance (Abs) at 450 nm, and increased absorbance corresponds to increased bound von Willebrand Factor.

FIG. 4C is a bar graph depicting results for the ELISA of FIG. 4A using recombinant polypeptide comprising a modified extracellular domain of platelet glycoprotein Ibα including the C65S and K237V mutations (SEQ ID NO: 31). The first four samples on the x-axis correspond to samples with known type 1, type 2B, type 3, and type 1 von Willebrand Disease, respectively (i.e., GK1422 (1); GH1423 (2B); GK1419 (3); GK1425 (1)). The fifth and sixth samples are control samples comprising pooled human plasma (i.e., DG-C1; DG-C2). The seventh sample is a goat blood serum control (which lacks von Willebrand Factor). The eighth through seventeenth samples are human blood plasma samples without von Willebrand Disease ("normal"). The eighteenth to twenty-second samples correspond to a serial dilution of a reference standard of pooled human plasma from no dilution (1:1) to 16-fold dilution (1:16). The y-axis corresponds to absorbance (Abs) at 450 nm, and increased absorbance corresponds to increased bound von Willebrand Factor.

FIG. 4D is a bar graph depicting results for the ELISA of FIG. 4A using recombinant polypeptide comprising a modified extracellular domain of platelet glycoprotein Ibα including the C65S and G233T mutations (SEQ ID NO: 21). The first four samples on the x-axis correspond to samples with known type 1, type 2B, type 3, and type 1 von Willebrand Disease, respectively (i.e., GK1422 (1); GH1423 (2B); GK1419 (3); GK1425 (1)). The fifth and sixth samples are control samples comprising pooled human plasma (i.e., DG-C1; DG-C2). The seventh sample is a goat blood serum control (which lacks von Willebrand Factor). The eighth through seventeenth samples are human blood plasma samples without von Willebrand Disease ("normal"). The eighteenth to twenty-second samples correspond to a serial dilution of a reference standard of pooled human plasma from no dilution (1:1) to 16-fold dilution (1:16). The y-axis corresponds to absorbance (Abs) at 450 nm, and increased absorbance corresponds to increased bound von Willebrand Factor.

DETAILED DESCRIPTION

The following description is merely intended to illustrate various embodiments of the present disclosure. As such, the specific modifications discussed are not intended to be limiting. It will be apparent to one skilled in the art that various equivalents, changes, and modifications may be made without departing from the spirit or scope of the subject matters presented herein, and it is understood that such equivalent embodiments are to be included herein.

As used in this specification and the appended claims, the singular forms "a," "an" and "the" include plural references unless the content clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Each embodiment in this specification is to be applied mutatis mutandis to every other embodiment unless expressly stated otherwise.

The following terms, unless otherwise indicated, shall be understood to have the following meanings:

As used herein, the term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

As used herein, the term "nucleic acid" refers to any materials comprised of DNA or RNA. Nucleic acids can be made synthetically or by living cells.

As used herein, the term "polynucleotide" refers to a polymeric chain of nucleotides. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native inter-nucleoside bonds, or both. The nucleic acid can be in any topological conformation. For instance, the nucleic acid can be single-stranded, double-stranded, triple-stranded, quadruplexed, partially double-stranded, branched, hair-pinned, circular, or in a padlocked conformation.

As used herein, the term "protein" or refers to large biological molecules, or macromolecules, consisting of one or more chains of amino acid residues. Many proteins are enzymes that catalyze biochemical reactions and are vital to metabolism. Proteins also have structural or mechanical functions, such as actin and myosin in muscle and the proteins in the cytoskeleton, which form a system of scaffolding that maintains cell shape. Other proteins are important in cell signaling, immune responses, cell adhesion, and the cell cycle. However, proteins may be completely artificial or recombinant, i.e., not existing naturally in a biological system.

As used herein, the term "polypeptide" refers to both naturally-occurring and non-naturally-occurring proteins, and fragments, mutants, derivatives and analogs thereof. A polypeptide may be monomeric or polymeric. A polypeptide may comprise a number of different domains each of which has one or more distinct activities.

The terms "wild-type sequence" or "wild-type gene" are used interchangeably herein, to refer to a sequence that is native or naturally occurring in a host cell. In some embodiments, the wild-type sequence refers to a sequence of interest that is the starting point of a protein engineering project. The wild-type sequence may encode either a homologous or heterologous protein. A homologous protein is one the host cell would produce without intervention. A heterologous protein is one that the host cell would not produce but for the intervention.

The terms "modified sequence" and "modified genes" are used interchangeably herein to refer to a sequence that includes at least a substitution, deletion, insertion or interruption of naturally occurring nucleic acid sequence.

As used herein, the terms "mutant sequence" and "mutant gene" are used interchangeably and refer to a sequence that has an alteration in at least one codon occurring in a host cell's wild-type sequence. Said alteration in at least one codon is also called "mutation". The expression product of the mutant sequence is a protein with an altered amino acid sequence relative to the wild-type. The expression product may have an altered functional capacity (e.g., enhanced binding affinity).

The term "sample", as used herein, refers to any biological material obtained from a subject or patient. In one aspect, a sample can comprise blood, peritoneal fluid, CSF, saliva or urine. In other aspects, a sample can comprise whole blood, blood plasma, blood serum, B cells enriched from blood samples, and cultured cells (e.g., B cells from a subject). A sample can also include a biopsy or tissue sample including neural tissue. In still other aspects, a sample can comprise whole cells and/or a lysate of the cells.

Various aspects of the embodiments disclosed herein relate to new recombinant polypeptides comprising mutations to a glycoprotein Ibα extracellular domain, which are not known to occur in nature, that increase its binding affinity for vWF relative to wild-type in the absence of both the glycoprotein Ibα-V-IX complex and shear stress. Various aspects of the embodiments disclosed herein relate to recombinant polypeptides comprising a glycoprotein Ibα extracellular domain and an oligomerization domain that increases the binding affinity of the recombinant polypeptide for vWF relative to polypeptides lacking an oligomerization domain in the absence of both the glycoprotein Ibα-V-IX complex and shear stress.

Various aspects of the embodiments relate to the determination that the novel, recombinant polypeptides disclosed herein are both capable of robust expression and proper folding and amenable to complex functional assays. In particular, many of the recombinant polypeptides disclosed herein are capable of distinguishing small defects in coagulation and attributing these defects to vWF.

I. Recombinant Polypeptides

Various aspects of the embodiments relate to a recombinant polypeptide that specifically binds human von Willebrand Factor (vWF) comprising a modified extracellular domain of platelet glycoprotein Ibα (GPIbα).

The term "specifically binds" refers to an interaction having a dissociation constant (Kd) of no more than 10 µM, such as either no more than about 6 µM, 5 µM, 4 µM, 3 µM, 2 µM, 1 µM, 950 nM, 900 nM, 850 nM, 800 nM, 750 nM, 700 nM, 650 nM, 600 nM, 550 nM, 500 nM, 450 nM, 400 nM, 350 nM, 300 nM, 250 nM, 200 nM, 150 nM, 100 nM, 90 nM, 80 nM, 70 nM, 60 nM, or 50 nM, or less than about 10 µM, 6 µM, 5 µM, 4 µM, 3 µM, 2 µM, 1 µM, 950 nM, 900 nM, 850 nM, 800 nM, 750 nM, 700 nM, 650 nM, 600 nM, 550 nM, 500 nM, 450 nM, 400 nM, 350 nM, 300 nM, 250 nM, 200 nM, 150 nM, 100 nM, 90 nM, 80 nM, 70 nM, 60 nM, or 50 nM, e.g., under physiological conditions, such as in human blood plasma or in HEPES or phosphate buffer, and, e.g., between the recombinant polypeptide (or an oligomeric polypeptide thereof) and wild-type human vWF. Whether a recombinant polypeptide specifically binds human vWF with a specific dissociation constant can be determined, for example, by fluorescence anisotropy or surface plasmon resonance as described herein, infra.

A recombinant polypeptide typically has a length of about 250 amino acids to about 1000 amino acids such as about 250 to about 550, about 500 to about 750, about 600 to about 800, about 750 to about 1000, about 250 to about 300, about 290 to about 350, about 300 to about 400, about 350 to about 450, about 400 to about 500, about 450 to about 550, about 500 to about 600 amino acids, about 550 to about 650, about 600 to about 700, about 650 to about 750, about 700 to about 800, about 750 to about 850, about 800 to about 900, about 850 to about 950, or about 900 to about 1000 amino acids.

A recombinant polypeptide typically has a molecular weight of about 25 kilodaltons (kDa) to about 100 kDa such as about 25 to about 55, about 50 to about 75, about 60 to about 80, about 75 to about 100, about 25 to about 30, about 29 to about 35, about 30 to about 40, about 35 to about 45, about 40 to about 50, about 45 to about 55, about 50 to about 60 amino acids, about 55 to about 65, about 60 to about 70, about 65 to about 75, about 70 to about 80, about 75 to about 85, about 80 to about 90, about 85 to about 95, or about 90 to about 100 kDa.

A recombinant polypeptide of the sort disclosed herein may have the amino acid sequence set forth in SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; or SEQ ID NO: 41. A recombinant polypeptide of the sort disclosed herein may have an amino acid sequence that has at least about 85%, 86%, 87%, 88%, 89%, 90%, 91%, 92%, 93%, 94%, 95%, 96%, 97%, 98%, 99%, or 99.5% sequence identity with the amino acid sequence set forth in SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; or SEQ ID NO: 41, i.e., wherein the complete amino acid sequence of the recombinant polypeptide is not a naturally-occurring amino acid sequence.

A. Modified Extracellular Domains

Modified extracellular domains of GPIbα are vWF-binding domains of GPIbα, corresponding to the amino acid sequence set forth in SEQ ID NO: 19, or a subsequence thereof, which contain one or more mutations including at least one "gain-of-function" or "loss-of-function" mutation. Gain-of-function and loss-of-function mutations increase or decrease, respectively, the binding affinity of the modified extracellular domain for vWF relative to a wild-type extracellular domain that spans the same amino acid sequence of GPIbα as the modified extracellular domain. Gain-of-function mutations that are not known to occur in nature include G233T, D235V, and K237V (i.e., wherein the amino acids are numbered as in SEQ ID NO: 19). Loss-of-function mutations that are not known to occur in nature include A238V or Δ(229-240) (i.e., as numbered in SEQ ID NO: 19).

A modified extracellular domain of GPIbα can include one or more mutations selected from G233T, D235V, and K237V. In some embodiments, the recombinant polypeptide or an oligomeric polypeptide thereof has a higher binding affinity for the vWF of a human blood sample or a human blood plasma sample than a control polypeptide that both (a) comprises the same subsequence of GPIbα as the recombinant polypeptide and (b) lacks the one or more mutations (e.g., wherein the recombinant polypeptide and control polypeptide are identical except for the presence of the one or more mutations in the recombinant polypeptide and the lack of the one or more mutations in the control polypeptide). In some embodiments, the Kd of the recombinant polypeptide or an oligomeric polypeptide thereof and human vWF is less than 4 µM, 3 µM, 2 µM, 1 µM, 950 nM, 900 nM, 850 nM, 800 nM, 750 nM, 700 nM, 650 nM, 600 nM, 550 nM, 500 nM, 450 nM, 400 nM, 350 nM, 300 nM, 250 nM, 200 nM, 150 nM, 100 nM, 90 nM, 80 nM, 70 nM, 60 nM, or 50 nM, e.g., under physiological conditions, such as in human blood plasma or in HEPES or phosphate buffer. The Kd may be determined, for example, either by a fluorescence anisotropy analysis of fluorescently-labelled vWF and recombinant polypeptide bound to slow-tumbling particles or by a surface plasmon resonance analysis of surface-bound vWF and soluble recombinant polypeptide, although a number of different methods are also useful to determine the Kd between a recombinant polypeptide or oligomeric polypeptide thereof and vWF.

A modified extracellular domain of GPIbα may include the A238V mutation.

A modified extracellular domain typically includes sufficient primary structure of human GPIbα to specifically bind human vWF. A modified extracellular domain can have, for example, at least about 95%, 96%, 97%, 98%, 99%, or 99.5% sequence identity with at least about 250, 260, 270, 280, or 290 consecutive amino acids of the amino acid sequence set forth in SEQ ID NO: 19. A modified extracellular domain can have at least about 95%, 96%, 97%, 98%, 99%, or 99.5% sequence identity with at least about 250, 260, 270, 280, or 290 consecutive amino acids of the amino acid sequence set forth in SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; or SEQ ID NO: 42. A modified extracellular domain can have 100% sequence identity with at least about 250, 260, 270, 280, or 290 consecutive amino acids of the amino acid sequence set forth in SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; or SEQ ID NO: 42. A modified extracellular domain can have at least about 95%, 96%, 97%, 98%, 99%, or 99.5% sequence identity with the amino acid sequence set forth in SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; or SEQ ID NO: 42. A modified extracellular domain can have the amino acid sequence set forth in SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; or SEQ ID NO: 42.

A modified extracellular domain typically includes secondary and tertiary structure similar to the wild type human GPIbα vWF-binding domain, including the intramolecular disulfide bonding pattern of wild type human GPIbα. The secondary and tertiary structure of wild type human GPIbα exists in a dynamic equilibrium between conformations that have low affinity for vWF and conformations that have high affinity for vWF. In some embodiments, the modified extracellular domain favors conformations that have high affinity for vWF as assessed, for example, by the measurement of a dissociation constant between the recombinant polypeptide or oligomeric polypeptide thereof and vWF.

In some embodiments, a modified extracellular domain includes glycosylation and/or other post-translational modifications that are found in wild type human GPIbα proteins. In some embodiments, a modified extracellular domain corresponds to a glycoform of wild type human GPIbα that exists in nature.

A recombinant polypeptide typically lacks the intrinsically-disordered extracellular region corresponding to amino acids 291-517 of GPIbα, which follow the vWF-binding domain set forth in SEQ ID NO: 19. A recombinant polypeptide preferably lacks the transmembrane domain of GPIbα, corresponding to amino acids 518-540, which follow the intrinsically-disordered extracellular region. A recombinant polypeptide typically lacks any transmembrane domain. A recombinant polypeptide preferably lacks the cytosolic domain of GPIbα, which follows the transmembrane domain in naturally-occurring GPIbα.

In certain preferred embodiments, the modified extracellular domain comprises a mutation to C65 such as C65S or C65A (i.e., as the amino acid C65 is numbered in SEQ ID NO: 19).

A modified extracellular domain may include, for example, mutations C65S and G233T, mutations C65S and D235V, mutations C65S and K237V, or mutations C65S, G233T, and M239T.

A modified extracellular domain may include, for example, mutations C65A, G233V and M239V. In some embodiments, the modified extracellular domain comprises the amino acid sequence set forth in of SEQ ID NO: 42.

In some embodiments, the modified extracellular domain includes a mutation of a wild type GPIbα amino acid to a β-branched amino acid (e.g., valine or threonine), wherein the wild type GPIbα amino acid is not a β-branched amino acid. In some embodiments, the modified extracellular domain includes a mutation of a wild type GPIbα amino acid to an amino acid comprising a hydroxyl (e.g., threonine), wherein the wild type GPIbα amino acid does not comprise a hydroxyl. In some embodiments, the modified extracellular domain includes a mutation of a wild type GPIbα amino acid to a β-branched amino acid comprising a hydroxyl (e.g., threonine), wherein the wild type GPIbα amino acid is not a β-branched amino acid comprising a hydroxyl.

In some embodiments, the modified extracellular domain includes a mutation that is not known to occur in nature.

In some embodiments, the modified extracellular domain has an electrostatic charge at physiological pH that differs from the electrostatic charge of a wild type extracellular domain that spans the same stretch of amino acids as the modified extracellular domain (e.g., wherein the electrostatic charge differs from wild type by at least about 0.5 such as by about 1.0).

In some embodiments, the modified extracellular domain includes a mutation of a wild type GPIbα amino acid to an amino acid that has lower conformational entropy than the wild-type amino acid such as a mutation of glycine to threonine.

In some embodiments, the modified extracellular domain lacks one or more mutations selected from mutation to amino acid number 226, 227, 228, 229, 230, 231, 232, 233, 234, 235, 236, 237, 238, 239, 240, 241, 242, 243, or 244 of SEQ ID NO: 19.

In some embodiments, the modified extracellular domain lacks one or more mutations selected from C65A, N226V, Y228V, W230L, K231V, Q232V, G233V, G233S, D235V, D235Y, K237V, A238V, M239S, M239V, M239I, T240V, and A244V.

In some embodiments, the modified extracellular domain comprises the A238V mutation, and the recombinant polypeptide has a lower binding affinity for the vWF of a human blood sample or a human blood plasma sample than a control polypeptide that both (a) comprises the same subsequence of GPIbα as the recombinant polypeptide and (b) lacks the A238V mutation (e.g., wherein the recombinant polypeptide and control polypeptide are identical except for the presence of the A238V mutation in the recombinant polypeptide and the lack of the A238V mutation in the control polypeptide). In some embodiments, the modified extracellular domain comprises the amino acid sequence set forth in of SEQ ID NO: 6.

In some embodiments, the modified extracellular domain comprises the deletion of amino acids 229 to 240 (Δ(229-240) mutation), relative to SEQ ID NO: 19, and the recombinant polypeptide has a lower binding affinity for the vWF of a human blood sample or a human blood plasma sample than a control polypeptide that both (a) comprises the same subsequence of GPIbα as the recombinant polypeptide and (b) lacks the Δ(229-240) mutation (e.g., wherein the recombinant polypeptide and control polypeptide are identical except for the presence of the Δ(229-240) mutation in the recombinant polypeptide and the lack of the Δ(229-240) mutation in the control polypeptide). In some embodiments, the modified extracellular domain comprises the amino acid sequence set forth in of SEQ ID NO: 9.

B. Cross-Linking Domains

Various aspects of the embodiments relate to a recombinant polypeptide comprising a cross-linking domain. A cross-linking domain typically allows for the recombinant polypeptide to be covalently or non-covalently cross-linked to a soluble molecule or solid support.

The inventors have found and disclose that traditional chemistries to randomly cross-link primary amines (e.g., lysine) or carboxyls (e.g., aspartate, glutamate, C-terminus) of a recombinant polypeptide to solid supports or other components of an assay such as by 1-ethyl-3-(-3-dimethylaminopropyl) carbodiimide (EDAC) or N-hydroxysuccinimide (NHS) chemistries result in functional defects, which reduce assay accuracy and precision. Random cross-linking is often a superior strategy for assay development because random cross-linking provides a population of cross-linked molecules in multiple different orientations, which allows for interactions between each surface of the cross-linked molecules and their binding partners in an assay. Directional cross-linking is often inferior to random cross-linking for assay development because directional cross-linking masks a surface of the cross-linked molecule, particularly when the molecule is cross-linked to a solid support, and may affect the structure and dynamics of each molecule in a uniform way, as well as their interactions with binding partners, thereby introducing systematic error into an assay. Directional cross-linking is also generally laborious and expensive relative to random cross-linking, for example, because directional cross-linking requires both the design, cloning, expression, and analysis of recombinant polypeptide and the validation of assays that utilize the directionally-cross-linked recombinant polypeptide with no guarantee that any design will avoid systematic error.

Various aspects of the embodiments relate to the finding that the cross-linking of a recombinant polypeptide as described herein to a solid support as mediated by the C-terminus of the recombinant polypeptide allows for assays with superior precision and accuracy relative to random cross-linking.

In some embodiments, a recombinant polypeptide comprises a cross-linking domain. The cross-linking domain may optionally comprise a negatively-charged C-terminal domain. A negatively-charged C-terminal domain typically includes a stretch of 3 to 20 amino acids (i.e., 3, 4, 5, 6, 7, 8, 9, 10, 11, 12, 13, 14, 15, 16, 17, 18, 19, or 20 amino acids) that has a net negative charge at neutral pH such as a net charge less than about −1, −2, −3, −4, −5, or −6. The term "negatively-charged C-terminal domain" does not necessarily mean that the amino acid sequence of the negatively-charged C-terminal domain includes the amino acid of the C-terminus of a recombinant polypeptide, although a negatively-charged C-terminal domain may include the C-terminal amino acid. "C-terminal" instead refers to the positioning of the negatively-charged domain relative to the modified extracellular domain of platelet glycoprotein Ibα in a recombinant polypeptide, i.e., a negatively-charged C-terminal domain is C-terminal relative to the modified extracellular domain.

The negatively-charged C-terminal domain typically includes amino acids such as glutamate and aspartate (e.g., at least 3, 4, 5, 6, 7, 8, 9, or 10 glutamates and aspartates) and lacks amino acids such as arginine, lysine, and histidine (e.g., not more than 6, 5, 4, 3, 2, or 1 arginines lysines, and histidines). The negatively-charged C-terminal domain may also optionally include small, hydrophilic amino acids that display a high degree of conformational entropy (e.g., glycine, alanine, serine) and/or proline, which are useful to disfavor secondary structure.

In some embodiments, the cross-linking domain may comprise a negatively-charged C-terminal domain and an affinity tag. In some embodiments the affinity tag is a polyhistidine tag. In recombinant polypeptides that include both a polyhistidine tag and a negatively-charged C-terminal domain, the negatively-charged C-terminal domain is typically positioned between the modified extracellular domain and the polyhistidine tag. An example of an amino acid sequence that includes a negatively-charged C-terminal domain and a polyhistidine tag is shown in SEQ ID NO: 17.

In recombinant polypeptides that include both an affinity tag and a negatively-charged C-terminal domain, the negatively-charged C-terminal domain is typically positioned between the modified extracellular domain and the affinity tag.

A cross-linking domain can optionally comprise a C-terminal cysteine. C-terminal cysteines are useful to cross-link recombinant polypeptides to a solid support or other component of an assay, for example, using thiol-maleimide chemistry or a thiol-gold interaction. In some embodiments, the cross-linking domain may comprise a C-terminal cysteine and an affinity tag. In some embodiments the affinity tag is a polyhistidine tag. An example of an amino acid sequence comprising a polyhistidine tag and a C-terminal cysteine is set forth in SEQ ID NO: 16.

The term "C-terminal cysteine" does not necessarily mean that the C-terminal cysteine is the C-terminal amino acid of a recombinant polypeptide, although a C-terminal cysteine may be the C-terminal amino acid. "C-terminal" instead refers to the positioning of the C-terminal cysteine relative to the modified extracellular domain of platelet glycoprotein Ibα in a recombinant polypeptide, i.e., a C-terminal cysteine is C-terminal relative to the modified extracellular domain.

A cross-linking domain can optionally comprise a streptavidin binding protein or a functional equivalent thereof. Streptavidin binding protein is useful to non-covalently cross-link recombinant polypeptides to streptavidin. In some embodiments, the cross-linking domain may comprise a streptavidin binding protein and an affinity tag. In some embodiments the affinity tag is a polyhistidine tag. An example of an amino acid sequence comprising streptavidin binding protein and a polyhistidine tag is set forth in SEQ ID NO: 18.

In some embodiments, the cross-linking domain may comprise the Fc domain of an antibody. An example of an amino acid sequence comprising the Fc domain of an antibody is set forth in SEQ ID NO: 11 or SEQ ID NO: 12.

A cross-linking domain according to the present invention may have the amino acid sequence set forth in SEQ ID NO: 11; SEQ ID NO: 12, SEQ ID NO: 16; SEQ ID NO: 17; or SEQ ID NO: 18.

C. Affinity Tags

A recombinant polypeptide may optionally include an affinity tag. Affinity tags are useful for purification, and they may also be useful in assays that utilize a recombinant polypeptide. Exemplary affinity tags include polyhistidine tag, Snap tag, Clip tag, HaloTag, SnoopTag, SpyTag, chitin binding protein, maltose binding protein, Strep-tag, glutathione-S-transferase, FLAG-tag, V5-tag, Myc-tag, HA-tag, NE-tag, AviTag, Calmodulin-tag, polyglutamate, S-tag, SBP-tag, Softag 1, Softag 3, TC tag, VSV-tag, Xpress tag, Isopeptag, biotin carboxyl carrier protein, green fluorescent protein-tag, Nus-tag, thioredoxin-tag and the Fc domain of an antibody, although the choice of affinity tag is not particularly limiting. A recombinant polypeptide may nevertheless lack an affinity tag, for example, if the affinity tag is removed after use or if the recombinant polypeptide is purified using a strategy that does not require an affinity tag. An exemplary affinity tag is polyhistidine tag, which typically includes an amino acid sequence comprising six or eight consecutive histidines although the number of histidines residues is not particularly limiting (see, e.g., SEQ ID NO: 15-18, 43, 44, 46). In some embodiments, the affinity tag may comprise a glycine linker (see e.g. SEQ ID NO: 44). In some embodiments, the affinity tag may comprise the Fc domain of an antibody (see e.g. SEQ ID NO: 46). In some embodiments, the affinity tag is the Fc domain of an antibody (see e.g. SEQ ID NO: 11 or 12).

An affinity tag according to the present invention can have the amino acid sequence set forth in SEQ ID NO: 11; SEQ ID NO: 12; SEQ ID NO: 15; SEQ ID NO: 16; SEQ ID NO: 17; SEQ ID NO: 18; SEQ ID NO: 43; SEQ ID NO: 44; SEQ ID NO: 45; or SEQ ID NO: 46.

C. Oligomerization Domains

A recombinant polypeptide may optionally comprise an oligomerization domain. An oligomerization domain allows for the formation of oligomers such as dimers, trimers, tetramers, pentamers, and/or higher-order oligomers. An oligomerization domain may favor a specific stoichiometry, e.g., dimers, trimers, tetramers, or pentamers, or an oligomerization domain may allow for a distribution of oligomers having different stoichiometries. An oligomerization domain may be designed to form homo-oligomers, although the distinction between homo-oligomers and hetero-oligomers is not particularly limiting. In some embodiments, the oligomerization domain is capable of forming a homo-dimer, homo-trimer, homo-tetramer, or homo-pentamer, e.g., wherein the oligomerization of a recombinant polypeptide results in a predominantly monodisperse oligomer. The oligomerization domain may be, for example, an oligomerization domain from p53, GCN4, clathrin, pent-tag, or the Fc domain of an antibody.

An oligomerization domain provides several advantages for recombinant polypeptides that are used in assays. An oligomerization domain can orient recombinant polypeptides relative to each other, which can approximate, for example, the orientation of native GPIbα in the lipid bilayer of a platelet. An oligomerization domain can also increase the affinity of a recombinant polypeptide for vWF, for example, because vWF is multi-valent, and the binding of the multiple modified extracellular domains of an oligomeric polypeptide to vWF has inherently higher binding affinity than the binding of a single modified extracellular domain to vWF.

An exemplary oligomerization domain includes the amino acid sequence of an antibody Fc domain hinge region. In addition to the benefits of oligomerization domains described above, Fc domains often increase the expression and/or secretion of a recombinant polypeptide in expression cells.

The species of an antibody Fc domain may be selected based on the desired use of a recombinant polypeptide or oligomeric polypeptide. For example, the species of antibody Fc domain may be selected such that a specific reagent either targets or ignores the antibody Fc domain in an assay. A mouse Fc domain may be useful, for example, if no anti-mouse secondary antibody is used to detect other mouse antibodies in an assay. Similarly, a mouse Fc domain may be useful to cross-link a recombinant polypeptide to a solid support or other component of an assay using an anti-mouse antibody. The species of Fc domain may be human, mouse, rabbit, rat, hamster, guinea pig, goat, sheep, horse, chicken, or a chimera of any of the foregoing species, although the species of Fc domain is not particularly limiting.

An exemplary oligomerization domain is the mouse IgG Fc domain comprising the hinge region, which allows for recombinant polypeptides comprising the oligomerization domain to form a covalent homodimer. A dimeric mouse IgG Fc domain may have the amino acid sequence set forth in SEQ ID NO: 11 or SEQ ID NO: 12 or an amino acid sequence having at least about 95%, 96%, 97%, 98%, or 99% sequence identity with the amino acid sequence set forth in SEQ ID NO: 11 or SEQ ID NO: 12.

Fc domains may also aid the purification of a recombinant polypeptide as methods of purifying polypeptides comprising Fc domains are well known. Fc domains may also act as cross-linking domains. Fc domains may also act as affinity tags.

Another exemplary oligomerization domain is the p53 tetramerization domain. A p53 tetramerization domain may have the amino acid sequence set forth in SEQ ID NO: 10 or an amino acid sequence having at least about 95%, 96%, 97%, 98%, or 99% sequence identity with the amino acid sequence set forth in SEQ ID NO: 10.

Another exemplary oligomerization domain is the GCN4 trimerization domain. A GCN4 trimerization domain may have the amino acid sequence set forth in SEQ ID NO: 13 or an amino acid sequence having at least about 95%, 96%, 97%, 98%, or 99% sequence identity with the amino acid sequence set forth in SEQ ID NO: 13. A recombinant polypeptide comprising a GCN4-like sequence may be designed, for example, to be a parallel trimer. Alternate GCN4-like sequences may be designed as known in the art to prepare dimeric, trimeric, and tetrameric oligomers with either parallel or anti-parallel organization according methods known in the art (see, e.g., Harbury, Zhang, Kim, and Alber, "A switch between two-, three-, and four-stranded coiled coils in GCN4 leucine zipper mutants", Science (1993) 262:1401).

Another exemplary oligomerization domain is the clathrin trimerization domain. A clathrin trimerization domain may have the amino acid sequence set forth in SEQ ID NO: 14 or an amino acid sequence having at least about 95%, 96%, 97%, 98%, or 99% sequence identity with the amino acid sequence set forth in SEQ ID NO: 14.

In some embodiments, the oligomerization domain may include an affinity tag.

An oligomerization domain according to the present invention can have the amino acid sequence set forth in SEQ ID NO: 10; SEQ ID NO: 11; SEQ ID NO: 12; SEQ ID NO: 13; SEQ ID NO: 14; or SEQ ID NO: 46.

In some embodiments, the dissociation constant (Kd) between vWF and a recombinant polypeptide comprising an oligomerization domain is less than the dissociation constant between vWF and a control polypeptide both (a) comprising the same subsequence of GPIbα or mutant subsequence thereof as the recombinant polypeptide and (b) lacking the oligomerization domain (e.g., wherein the control polypeptide and the recombinant polypeptide are identical except for the presence of the oligomerization domain in the recombinant polypeptide and the lack of the oligomerization domain in the control polypeptide). The difference in dissociation constant (Kd) between such recombinant polypeptides and control polypeptides is typically attributable primarily or solely to the oligomerization states of the recombinant polypeptides and control polypeptides.

Other oligomerization domains are known in the art, and the specific choice of oligomerization domain is not particularly limiting. Streptavidin, for example, may be a particularly useful oligomerization domain because it forms a tetramer and also binds biotin, which may aid purification and which may also be useful in various assays.

D. Leader Peptide Sequences

Recombinant polypeptides disclosed herein typically comprise a leader peptide sequence to favor translocation of the recombinant polypeptide across the cell membrane of an expression vector, such as a mammalian cell, such as a human cell. A recombinant polypeptide may nevertheless lack a leader peptide sequence, for example, if the leader peptide sequence is cleaved from the recombinant polypeptide by enzymatic or chemical cleavage. Synthetically-produced recombinant polypeptides may similarly lack a leader peptide sequence.

A leader peptide sequence is typically included at the N-terminus of a recombinant polypeptide. A leader peptide sequence is preferably sufficient to translocate the recombinant polypeptide outside of the cell surface membrane of a eukaryotic cell (e.g., a mammalian cell, such as a human cell) following the translation of the recombinant polypeptide in the eukaryotic cell, although other sequence motifs of a recombinant polypeptide may also aid translocation.

An exemplary leader peptide sequence has the amino acid sequence set forth in SEQ ID NO: 20, which is the human tissue plasminogen signal peptide. This well-characterized sequence is capable of translocating polypeptides out of both human cells and other mammalian cells.

II. Oligomeric Polypeptides

Various aspects of the embodiments relate to an oligomeric polypeptide comprising 2, 3, 4, or more recombinant polypeptides (subunits) as described herein. In some embodiments, the oligomeric polypeptide is a dimeric polypeptide, i.e., an oligomeric polypeptide comprising two subunits, wherein each subunit is a recombinant polypeptide described herein. The term "polypeptide" as used without the modifiers "oligomeric," "dimeric," or other explicit reference to a multi-subunit form refers to a recombinant polypeptide that may or may not be present in an oligomer such as a dimer, trimer, or tetramer.

Each subunit of an oligomeric polypeptide typically has the same amino acid sequence, although different subunits of an oligomeric polypeptide may have different amino acid sequences. A heterodimeric polypeptide may be made, for example, by activating the cysteine thiols of a first subunit with a leaving group (e.g., with 2-2'dithio-bis-(5-nitropyridine)), reducing the thiols of a second subunit (e.g., with β-mercaptoethanol or tris(2-carboxyethyl)phosphine), and then contacting the first subunit and second subunit. Alternatively, the subunits may be randomly crosslinked and then purified. Homo-dimeric polypeptides may be made using similar strategies. Oligomeric polypeptides may be purified after oligomerization to separate the desired oligomeric polypeptide from monomeric subunits and other undesired species.

An oligomeric polypeptide may be symmetrical or the oligomeric polypeptide may lack symmetry. For example, an oligomeric polypeptide may form an "intermolecular" disulfide bonding pattern resulting in quaternary structure that lacks symmetry.

An oligomeric polypeptide may be crosslinked by noncovalent or covalent interactions. An example of a noncovalent interaction is the trimerization of a GCN4 or clathrin oligomerization domain or the tetramerization of a p53 oligomerization domain. An example of a covalent interaction is the disulfide-bond mediated dimerization of an antibody Fc domain hinge region. A dimeric polypeptide having subunits that include antibody Fc domains may be covalently crosslinked by at least one disulfide bond, typically 2 disulfide bonds (e.g., for $IgG_1$ and $IgG_4$ derived Fc domains) or 4 disulfide bonds (e.g., for $IgG_2$ derived Fc domains), although the number of disulfide bonds is not particularly limiting. $IgG_3$'s may be crosslinked, for example, with 11 disulfide bonds.

A dimeric polypeptide may comprise two subunits, wherein each subunit comprises an antibody Fc domain, and the antibody Fc domains crosslink the two subunits of the dimeric polypeptide.

A trimeric polypeptide may comprise three subunits, wherein each subunit comprises a GCN4 trimerization domain, and the GCN4 trimerization domains non-covalently crosslink the three subunits of the trimeric polypeptide. A trimeric polypeptide may comprise three subunits, wherein each subunit comprises a clathrin trimerization domain, and the clathrin trimerization domains non-covalently crosslink the three subunits of the trimeric polypeptide.

A tetrameric polypeptide may comprise four subunits, wherein each subunit comprises a p53 tetramerization domain, and the p53 tetramerization domains non-covalently crosslink the four subunits of the tetrameric polypeptide.

Various embodiments of the invention include a composition comprising a dimeric polypeptide, wherein the composition is essentially free of oligomeric polypeptides that are not dimeric polypeptides. A composition may lack oligomeric polypeptides that are not dimeric polypeptides.

Various embodiments of the invention include a composition comprising a trimeric polypeptide, wherein the composition is essentially free of oligomeric polypeptides that are not trimeric polypeptides. A composition may lack oligomeric polypeptides that are not trimeric polypeptides.

Various embodiments of the invention include a composition comprising a tetrameric polypeptide, wherein the composition is essentially free of oligomeric polypeptides that are not tetrameric polypeptides. A composition may lack oligomeric polypeptides that are not tetrameric polypeptides.

In some embodiments, a composition comprises a monomeric recombinant polypeptide, wherein the composition is essentially free of oligomeric polypeptides. A composition may lack oligomeric polypeptides.

III. Nucleic Acids, Cloning Cells, and Expression Cells

Embodiments described herein also include a nucleic acid comprising a nucleotide sequence encoding a modified extracellular domain (e.g., SEQ ID NO: 1-9, or 42) and/or a recombinant polypeptide described herein. The nucleic acid may be DNA or RNA. DNA comprising a nucleotide sequence encoding a recombinant polypeptide described herein typically comprises a promoter that is operably-linked to the nucleotide sequence. The promoter is preferably capable of driving constitutive or inducible expression of the nucleotide sequence in an expression cell of interest. The precise nucleotide sequence of the nucleic acid is not particularly limiting so long as the nucleotide sequence encodes a recombinant polypeptide described herein. Codons may be selected, for example, to match the codon bias of an expression cell of interest (e.g., a mammalian cell such as a human cell) and/or for convenience during cloning. DNA may be a plasmid, for example, which may comprise an origin of replication (e.g., for replication of the plasmid in a prokaryotic cell).

Various aspects of the embodiments relate to a cell comprising a nucleic acid comprising a nucleotide sequence that encodes a modified extracellular domain and/or recombinant polypeptide described herein. The cell may be an expression cell or a cloning cell. Nucleic acids are typically cloned in *E. coli*, although other cloning cells may be used. If the cell is an expression cell, the nucleic acid is optionally a nucleic acid of a chromosome, i.e., wherein the nucleotide sequence is integrated into the chromosome, although then nucleic acid may be present in an expression cell, for example, as extrachromosomal DNA.

Various aspects of the embodiments relate to a cell comprising a recombinant polypeptide or oligomeric polypeptide (e.g., dimeric, trimeric, or tetrameric polypeptide) as described herein. Various aspects of the embodiments relate to a composition comprising cells, cell culture media, and a recombinant polypeptide or oligomeric polypeptide as described herein, wherein the cells comprise a nucleic acid encoding the recombinant polypeptide or the subunits of the oligomeric polypeptide and the cell culture media comprises the recombinant polypeptide or oligomeric polypeptide (e.g., because the cells secreted the recombinant polypeptide or oligomeric polypeptide into the cell culture media). The cell is typically an expression cell. The nature of the expression cell is not particularly limiting. Mammalian expression cells may allow for favorable folding, post-translational modifications, and/or secretion of a recombinant polypeptide or oligomeric polypeptide, although other eukaryotic cells or prokaryotic cells may be used as expression cells. Exemplary expression cells include CHO, HEK, BHK, NS0, Sp2/0, COS, C127, HT-1080, PER.C6, HeLa, and Jurkat cells.

IV. Compositions and Methods Related to Assays

Various aspects of the invention relate to compositions comprising a recombinant polypeptide or oligomeric polypeptide as described herein, wherein the recombinant polypeptide or oligomeric polypeptide is directly or indirectly bound to a solid support. The term "direct" binding, as used herein, refers to the direct conjugation of a molecule to a solid support, e.g., a gold-thiol interaction that binds a cysteine thiol of a recombinant polypeptide to a gold surface. The term "indirect" binding, as used herein, includes the specific binding of a recombinant polypeptide to another molecule that is directly bound to a solid support, e.g., a recombinant polypeptide may bind an antibody that is directly bound to a solid support thereby indirectly binding the recombinant polypeptide to the solid support (see, e.g., FIG. 4A). The term "indirect" binding is independent of the number of molecules between the recombinant polypeptide and the solid support so long as (a) each interaction between the daisy chain of molecules is a specific or covalent interaction and (b) a terminal molecule of the daisy chain is directly bound to the solid support (see, e.g., FIG. 4A in which horseradish peroxidase (HRP), an anti-vWF antibody, vWF, and a recombinant polypeptide ("GPIbα") are each indirectly bound to a solid support through the direct binding of an anti-CD42b antibody to the solid support).

Various aspects of the invention relate to a composition comprising a recombinant polypeptide or oligomeric polypeptide as described herein, wherein the recombinant polypeptide or oligomeric polypeptide is covalently or non-covalently bound to a solid support. The term "non-covalently bound," as used herein, refers to specific binding such as between an antibody and its antigen, a ligand and its receptor, or an enzyme and its substrate, exemplified, for example, by the interaction between streptavidin binding protein and streptavidin or an antibody and its antigen (see, e.g., FIG. 4A). Specific binding generally refers to interactions with a dissociation constant (Kd) of less than about 10 μM, such as less than about 1 μM, less than about 100 nM, or less than about 10 nM.

A solid support may comprise a particle, a bead, a membrane, a surface, a polypeptide chip, a microtiter plate, or the solid-phase of a chromatography column. For example, the solid support may be a latex bead.

A composition may comprise a plurality of beads or particles, wherein each bead or particle of the plurality of beads or particles is directly or indirectly bound to at least one recombinant polypeptide or oligomeric polypeptide as described herein. A composition may comprise a plurality of beads or particles, wherein each bead or particle of the plurality of beads or particles is covalently or non-covalently bound to at least one recombinant polypeptide or oligomeric polypeptide as described herein.

A composition may comprise von Willebran Factor. A composition may comprise human vWF, e.g., in an aqueous solution or suspension such as whole blood or a fraction thereof such as blood plasma. A composition may comprise a solid support wherein the solid support comprises comprise a plurality of beads or particles, and the vWF cross-links the particles or beads of the plurality of particles or beads.

A composition may comprise human blood plasma. A composition may comprise human platelets. A composition may comprise human blood plasma and human platelets.

A composition may comprise an antibody, e.g., wherein the antibody is not a human antibody. The antibody may be, for example, a mouse, rabbit, rat, hamster, guinea pig, goat, sheep, horse, chicken, or a chimera of the foregoing species, although the species antibody is not particularly limiting. A composition may comprise an anti-vWF antibody, preferably an anti-human vWF antibody. A composition may comprise a fluorescently-labelled antibody. In some embodiments the anti-human vWF antibody is directly or indirectly bound to a dye, fluorophore or, enzyme.

A composition may comprise a pH buffer such as HEPES or phosphate buffer. A composition may comprise polyvinylpyrrolidone (PVP), Tween (e.g., Tween 20), or Dextran-500.

A composition may further comprise ristocetin. One advantage of the recombinant polypeptides disclosed herein is the development of assays that do not require ristocetin. In some embodiments, the compositions disclosed herein lack ristocetin Various aspects of the embodiments relate to a kit comprising a composition as described herein and instructions for use.

EXEMPLIFICATION

Example 1. Expression and Purification of Recombinant Polypeptides

The von Willebrand Factor (vWF)-binding domain of glycoprotein Ibα (GPIbα) consisting of 290 amino acids (SEQ ID NO: 19) was cloned with an N-terminal leader peptide from human tissue plasminogen activator (SEQ ID NO: 20) and a C-terminal polyhistidine tag (SEQ ID NO: 15, 16, 17, 18, 43, 44 or 46). Select amino acid mutations were introduced into the vWF-binding domain of GPIbα. Oligomerization domains and cross-linking domains were cloned into select constructs. The constructs were transiently or stably expressed in human embryonic kidney (HEK) cells or Chinese hamster ovary (CHO) cells. Recombinant polypeptide was purified from cell culture supernatant by immobilized metal affinity chromatography (IMAC) using a phosphate buffered saline (PBS) mobile phase comprising 0.02% sodium azide. Recombinant polypeptide purity was assessed by sodium dodecyl sulfate polyacrylamide gel electrophoresis (SDS-PAGE) under reducing conditions in 4-15% TGX™ polyacrylamide gels (Bio-Rad, California). Images of gels containing select recombinant polypeptide are shown in FIG. 1.

Example 2. Measurement of Binding Affinity (Kd) Between vWF and Recombinant Polypeptide The dissociation constants (Kd) between vWF and select dimeric polypeptides or a monomeric polypeptide control (G233V, M239V-noFc (SEQ ID NO: 35)) were assessed by fluorescence anisotropy. Each dimeric polypeptide included two recombinant polypeptide subunits each comprising a murine Fc dimerization domain and a modified extracellular domain of GPIbα. The dimeric polypeptides assessed correspond to SEQ ID NO: 38 (Δ(229-240)); SEQ ID NO: 37 (WT); SEQ ID NO: 36 (A238V); SEQ ID NO: 34 (G233V, M239V); SEQ ID NO: 32 (G233V); SEQ ID NO: 33 (G233T, M239T); SEQ ID NO: 21 (G233T); SEQ ID NO: 30 (D235V); SEQ ID NO: 31 (K237V). The vWF A1 domain (amino acids 1277-1453 of human vWF), which specifically binds the GPIbα vWF-binding domain, was conjugated to the AlexaFluor™ 488 fluorescence label (Molecular Probes, Oregon) using cysteine-thiol-maleimide chemistry. Recombinant polypeptides were conjugated to slow-tumbling particles. A 2× serial dilution of each recombinant polypeptide from 5 μM to 9.75 nM was incubated for >30 minutes with 150 nM of the vWF A1-AlexaFluor™ 488 species at room temperature, and then fluorescence anisotropy was measured. Results are shown in FIG. 2. Recombinant polypeptide that did not include a mutation displayed a Kd of about 1.25 μM. Recombinant polypeptides that included one of the G233T, D235V, or K237V mutations each displayed Kds less than 500 nM (i.e., ~67 nM, ~250 nM, and ~300 nM, respectively, for single mutants). The relative binding affinity of the G233T, D235V, or K237V mutants was confirmed by ELISA (see FIGS. 4D, 4B and 4C respectively, and Example 3, infra).

Fluorescence anisotropy results were confirmed by surface plasmon resonance using Biacore™ (Biacore, Sweden) (FIG. 3). The vWF A1 domain was conjugated to a Biacore CM5 chip. The on- and off-rates of a recombinant polypeptide comprising the G233T mutation to the GPIbα extracellular domain, a C-terminal murine Fc domain, and a C-terminal 8-His tag (SEQ ID NO: 21) were measured, and the dissociation constant was calculated as ~58 nM, which is consistent with the ~67 nM measurement obtained by fluorescence anisotropy.

Example 3. Recombinant Polypeptide is Capable of Detecting Qualitative Defects in vWF Binding by ELISA Enzyme immunosorbent assays (ELISA) were used to determine that recombinant polypeptides comprising the G233T (SEQ ID NO: 21), D235V (SEQ ID NO: 30), and K237V (SEQ ID NO: 31) mutations are capable of detecting qualitative differences in vWF binding affinity. FIG. 4A displays a cartoon of the ELISA assay. Briefly, the wells of a multi-well plate were coated with an anti-CD42b antibody, which specifically binds the modified extracellular domain of GPIbα of the recombinant polypeptides and was used to indirectly cross-link the recombinant polypeptides to the multi-well plate (i.e., the solid support). Various control samples, standards, and serial dilutions thereof were added to different wells of the multi-well plate including plasma samples associated with type 1, type 2B, and type 3 von Willebrand Disease, control samples of pooled human blood plasma, control samples of human blood plasma known not to have von Willebrand Disease, a 2× serial dilution of a reference standard of pooled human plasma from no dilution to 16-fold dilution, and goat blood serum as a negative control. After incubation, the wells were washed and then contacted with a polyclonal rabbit anti-human vWF antibody, which was conjugated to horseradish peroxidase. Bound vWF was quantified by monitoring the conversion of a horseradish peroxidase substrate into product by absorption spectroscopy at 450 nm.

Each of the recombinant polypeptides comprising the G233T, D235V, or K237V mutations were capable of detecting the defects in the plasma samples associated with type 1, type 2B, and type 3 von Willebrand Disease, e.g., relative to normal plasma samples and control samples (FIG. 4B-4D). Each of the recombinant polypeptides comprising the G233T, D235V, and K237V mutations also allowed for accurate correlation between the five samples of the serial dilution and absorbance measurement. These results demonstrate that recombinant polypeptides described herein comprising at least one of the G233T, D235V, and K237V mutations can be used in assays for detecting von Willebrand Disease and that such assays can allow the accurate measurement of vWF concentration and/or binding affinity in plasma over a dynamic range that spans more than an order of magnitude.

REFERENCES

[1] U.S. Pat. No. 8,932,820
[2] U.S. Pat. No. 8,163,496
[3] J. L. Miller, D. Cunningham, V. A. Lyle, and C. N. Finch, "Mutation in the gene encoding the a chain of platelet glycoprotein Ib in platelet-type von Willebrand disease," Proc. Natl. Acad. Sci. U.S.A, vol. 88, no. June, pp. 4761-4765, 1991.
[4] S. D. Russell and G. J. Roth, "Pseudo-von Willebrand Disease: A Mutation in the Platelet Glycoprotein Ibα Gene Associated With a Hyperactive Surface Receptor," Blood, vol. 81, no. 7, pp. 1787-1792, 1993.
[5] A. Hamilton et al., "Frequency of Platelet type versus Type 2B von Willebrand Disease An international registry-based study," Thromb. Haemost., vol. 105, pp. 501-508, 2011.
[6] S. Enayat et al., "A novel D235Y mutation in the GP1BA gene enhances platelet interaction with von Willebrand factor in an Iranian family with platelet-type von Willebrand disease," Thromb. Haemost., vol. 108, no. 5, pp. 946-954, 2012.
[7] A. I. Woods et al., "Identification of p.W246L As a Novel Mutation in the GP1BA Gene Responsible for Platelet-Type von Willebrand Disease," Semin. Thromb. Hemost., vol. 40, pp. 151-160, 2014.
[8] C. Lavenu-bombled, C. Guitton, A. Dupuis, M. Baas, and C. Desconclois, "A novel platelet-type von Willebrand disease mutation (GP1BA p.Met255Ile) associated with type 2B ' Malmo/New York' von Willebrand disease," Thromb. Haemost., vol. 105, no. 3, pp. 501-8, 2016.
[9] J. Dong et al., "Novel Gain-of-Function Mutations of Platelet Glycoprotein Ib α by Valine Mutagenesis in the Cys209 Cys248 Disulfide Loop," Journal, vol. 275, no. 36, pp. 27663-70, 2000.

The invention claimed is:

1. A recombinant polypeptide that specifically binds human von Willebrand Factor, comprising a modified extracellular domain of platelet glycoprotein Ibα wherein:
the recombinant polypeptide lacks a transmembrane domain; and
the modified extracellular domain comprises at least one mutation selected from G233T, D235V, and K237V, relative to SEQ ID NO: 19,
wherein the modified extracellular domain comprises at least 250 consecutive amino acids of an amino acid sequence selected from the group consisting of: SEQ ID NO: 2; SEQ ID NO: 3; SEQ ID NO: 4; and SEQ ID NO: 5.

2. The recombinant polypeptide of claim 1, wherein the recombinant polypeptide has a higher binding affinity for the von Willebrand Factor of a human blood sample or human blood plasma sample than a control polypeptide that does not comprise the at least one mutation but that is otherwise identical to the recombinant polypeptide.

3. The recombinant polypeptide of claim 1, wherein the Kd of the recombinant polypeptide and human von Willebrand Factor is less than 1 μM, 750 nM, 500 nM, 250 nM, or 100 nM.

4. The recombinant polypeptide of claim 1, wherein the modified extracellular domain comprises:
mutations C65S and G233T;
mutations C65S and D235V;
mutations C65S and K237V; or
mutations C65S, G233T, and M239T, relative to SEQ ID NO: 19.

5. The recombinant polypeptide of claim 1, wherein the modified extracellular domain comprises an amino acid sequence selected from the group consisting of: SEQ ID NO: 2; SEQ ID NO: 3; SEQ ID NO: 4; and SEQ ID NO: 5.

6. The recombinant polypeptide of claim 1, further comprising a cross-linking domain, wherein the cross-linking domain comprises one or more of the group consisting of: a C-terminal cysteine, a negatively-charged C-terminal domain, and streptavidin binding protein.

7. The recombinant polypeptide of claim 6, wherein the amino acid sequence of the cross-linking domain is selected from the group consisting of: SEQ ID NO: 11; SEQ ID NO: 12; SEQ ID NO: 16; SEQ ID NO: 17; and SEQ ID NO: 18.

8. The recombinant polypeptide of claim 1, further comprising an affinity tag selected from the group consisting of: polyhistidine tag, Snap tag, Clip tag, HaloTag, SnoopTag, SpyTag, chitin binding protein, maltose binding protein, Strep-tag, glutathione-S-transferase, FLAG-tag, V5-tag, Myc-tag, HA-tag, NE-tag, Avi Tag, Calmodulin-tag, polyglutamate, S-tag, SBP-tag, Softag 1, Softag 3, TC tag, VSV-tag, Xpress tag, Isopeptag, biotin carboxyl carrier protein, green fluorescent protein-tag, Nus-tag, thioredoxin-tag and the Fc domain of an antibody.

9. The recombinant polypeptide of claim 8, wherein the affinity tag is a polyhistidine tag having from 6 to 8 histidine residues.

10. The recombinant polypeptide of claim 8, wherein the amino acid sequence of the affinity tag is selected from the group consisting of SEQ ID NO: 11; SEQ ID NO: 12; SEQ ID NO: 15; SEQ ID NO: 16; SEQ ID NO: 17; SEQ ID NO: 18; SEQ ID NO: 43, SEQ ID NO: 44; SEQ ID NO: 45; and SEQ ID NO: 46.

11. The recombinant polypeptide of claim 1, further comprising an oligomerization domain, wherein the oligomerization domain is capable of forming a dimer, trimer, tetramer, or pentamer.

12. The recombinant polypeptide of claim 11, wherein the oligomerization domain is selected from the group consisting of p53, GCN4, clathrin, pent-tag, or the Fc domain of an antibody.

13. The recombinant polypeptide of claim 11, wherein the amino acid sequence of the oligomerization domain is selected from the group consisting of SEQ ID NO: 10; SEQ ID NO: 11; SEQ ID NO: 12; SEQ ID NO: 13; SEQ ID NO: 14; and SEQ ID NO: 46.

14. The recombinant polypeptide of claim 1, wherein the amino acid sequence of the recombinant polypeptide has at least 95% sequence identity with an amino acid sequence selected from the group consisting of: SEQ ID NO: 21; SEQ ID NO: 22; SEQ ID NO: 24; SEQ ID NO: 25; SEQ ID NO: 30; SEQ ID NO: 31; SEQ ID NO: 33; SEQ ID NO: 39; SEQ ID NO: 40; and SEQ ID NO: 41.

15. The recombinant polypeptide of claim 1, wherein the amino acid sequence of the recombinant polypeptide is selected from the group consisting of: SEQ ID NO: 21; SEQ ID NO: 22; SEQ ID NO: 24; SEQ ID NO: 25; SEQ ID NO: 30; SEQ ID NO: 31; SEQ ID NO: 33; SEQ ID NO: 39; SEQ ID NO: 40; and SEQ ID NO: 41.

16. The recombinant polypeptide of claim 1, further comprising a leader peptide.

17. The recombinant polypeptide of claim 16, wherein the amino acid sequence of the leader peptide is SEQ ID NO: 20.

18. An oligomeric polypeptide, comprising at least two of the recombinant polypeptides according to claim 1.

19. A composition, comprising the recombinant polypeptide of claim 1, and a solid support, wherein the recombinant polypeptide or the oligomeric polypeptide is covalently or non-covalently bound to the solid support.

20. The composition of claim 19, wherein the solid support comprises a particle, a bead, a membrane, a surface, a polypeptide chip, a microtiter plate, or the solid-phase of a chromatography column.

21. The composition of claim 20, wherein the solid support is a latex particle.

22. The composition of claim 19, further comprising von Willebrand Factor.

23. The composition of claim 22, wherein:
the solid support comprises a plurality of particles or beads; and
the von Willebrand Factor cross-links the particles or beads of the plurality of particles or beads.

24. The composition of claim 22, further comprising human blood plasma.

25. The composition of claim 24, further comprising human platelets.

26. A recombinant polypeptide that specifically binds human von Willebrand Factor, comprising a modified extracellular domain of platelet glycoprotein Ibα wherein the amino acid sequence includes a mutation at position 233 and at position 65 or 239 relative to SEQ ID NO: 19, the mutation at position 233 is a G233T mutation, the mutation at position 65 is a C65A mutation, and the mutation at position 239 a M239V mutation and wherein the modified extracellular domain comprises at least 250 consecutive amino acids of an amino acid sequence selected from the group consisting of: SEQ ID NO: 2; SEQ ID NO: 3; SEQ ID NO: 4; and SEQ ID NO: 5.

* * * * *